US006936592B2

(12) United States Patent
Bronk et al.

(10) Patent No.: US 6,936,592 B2
(45) Date of Patent: *Aug. 30, 2005

(54) 4"-SUBSTITUTED-9-DEOXO-9A-AZA-9A-HOMOERYTHROMYCIN A DERIVATIVES

(75) Inventors: Brian Scott Bronk, Gales Ferry, CT (US); Michael Anthony Letavic, Mystic, CT (US)

(73) Assignee: Pfizer, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/810,922

(22) Filed: Mar. 26, 2004

(65) Prior Publication Data

US 2004/0180842 A1 Sep. 16, 2004

Related U.S. Application Data

(63) Continuation of application No. 10/273,879, filed on Oct. 18, 2002, now Pat. No. 6,777,393, which is a continuation of application No. 09/989,936, filed on Nov. 21, 2001, now abandoned, which is a continuation of application No. 09/424,104, filed as application No. PCT/IB98/00839 on May 29, 1998, now Pat. No. 6,420,536.

(60) Provisional application No. 60/049,348, filed on Jun. 11, 1997.

(51) Int. Cl.[7] .............................................. A61K 31/79
(52) U.S. Cl. ..................................... 514/29; 536/7.4
(58) Field of Search .............................. 514/7.4; 536/29

(56) References Cited

FOREIGN PATENT DOCUMENTS

| EP | 0508699 A | 4/1992 | ........... C07H/17/08 |
| EP | 0549040 | 12/1992 | ........... C07H/17/08 |
| WO | WO 98/56802 | 12/1998 | ........... C07H/17/08 |
| WO | WO 00/31097 | 6/2000 | ........... C07H/17/08 |

Primary Examiner—Elli Peselev
(74) Attorney, Agent, or Firm—Charles W. Ashbrook; Thomas A. Wootton

(57) ABSTRACT

The invention relates to a method of preparing compounds of the formula

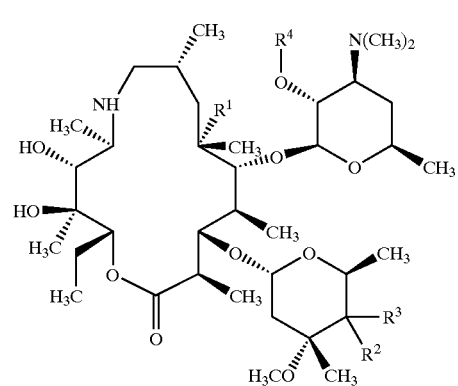

and to pharmaceutically acceptable salts thereof. The compounds of formula 1 are antibacterial agents that may be used to treat various bacterial and protozoa infections. The invention also relates to pharmaceutical compositions containing the compounds of formula 1 and to methods of treating bacterial protozoa infections by administering the compounds of formula 1. The invention also relates to methods of preparing the compounds of formula 1 and to intermediates useful in such preparation.

1 Claim, No Drawings

US 6,936,592 B2

4"-SUBSTITUTED-9-DEOXO-9A-AZA-9A-HOMOERYTHROMYCIN A DERIVATIVES

CROSS REFERENCE TO RELATED APPLICATIONS

This application is a continuation of U.S. Pat. No. 6,777,393 dated Aug. 17,2004, filed as U.S. patent application Ser. No. 10/273,879 on Oct. 18,2002, which is a continuation of U.S. patent application Ser. No. 09/989,936, filed on Nov. 21, 2001, now abandoned, which is a continuation of U.S. patent application Ser. No, 09/424,104, filed on Nov. 18, 1999, now U.S. Pat. No. 6,420,536, which is the National Stage of International Application No. PCT/IB98/00839, filed on May 29. 1998, which claims the benefit of U.S. Provisional Application No. 60/049,348 filed on Jun. 11, 1997; all of which are incorporated in their entirety herein by reference.

BACKGROUND OF THE INVENTION

This invention relates to novel C-4" substituted derivatives of 9-deoxo-9a-aza-9a-homoerythromycin A that are useful as antibacterial and antiprotozoa agents in mammals, including man, as well as in fish and birds. This invention also relates to pharmaceutical compositions containing the novel compounds and to methods of treating bacterial infections and protozoa infections in mammals, fish and birds by administering the novel compounds to mammals, fish and birds requiring such treatment.

Macrolide antibiotics are known to be useful in the treatment of a broad sprectrum of bacterial infections and protozoa infections in mammals, fish and birds. Such antibiotics include various derivatives of erythromycin A such as azithromycin which is commercially available and is referred to in U.S. Pat. Nos. 4,474,768 and 4,517,359, both of which are incorporated herein by reference in their entirety. Like azithromycin and other macrolide antibiotics, the novel macrolide compounds of the present invention possess potent activity against various bacterial infections and protozoa infections as described below.

SUMMARY OF THE INVENTION

The present invention relates to compounds of the formula

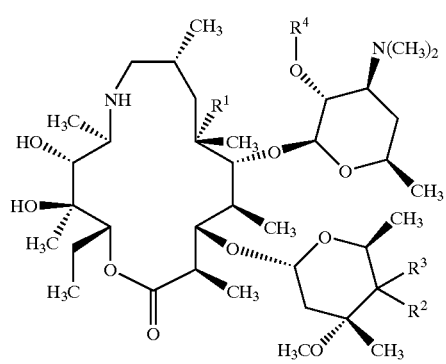

and to pharmaceutically acceptable salts thereof, wherein:

$R^1$ is H, hydroxy or methoxy;

$R^2$ is hydroxy;

$R^3$ is $C_1$–$C_{10}$ alkyl, $C_2$–$C_{10}$ alkenyl, $C_2$–$C_{10}$ alkynyl, cyano, —$CH_2S(O)_nR^8$ wherein n is an integer ranging from 0 to 2, —$CH_2OR^8$, —$CH_2N(OR^9)R^8$, —$CH_2NR^8R^{15}$, —$(CH_2)_m(C_8$–$C_{10}$ aryl), or —$(CH_2)_m$(5–10 membered heteroaryl), wherein m is an integer ranging from 0 to 4, and wherein the foregoing $R^3$ groups are optionally substituted by 1 to 3 $R^{16}$ groups;

or $R^2$ and $R^3$ are taken together to form an oxazolyl ring as shown below

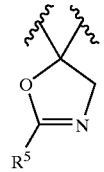

$R^4$ is H, —C(O)$R^9$, —C(O)O$R^9$, —C(O)NR$^9$R$^{10}$ or a hydroxy protecting group;

$R^5$ is —SR$^8$, —(CH$_2$)$_n$C(O)R$^8$ wherein n is 0 or 1, $C_1$–$C_{10}$ alkyl, $C_2$–$C_{10}$ alkenyl, $C_2$–$C_{10}$ alkynyl, —(CH$_2$)$_m$(C$_8$–$C_{10}$ aryl), or —(CH$_2$)$_m$(5–10 membered heteroaryl), wherein m is an integer ranging from 0 to 4, and wherein the foregoing $R^5$ groups are optionally substituted by 1 to 3 $R^{18}$ groups;

each $R^6$ and $R^7$ is independently H, hydroxy, $C_1$–$C_6$ alkoxy, $C_1$–$C_6$ alkyl, $C_2$–$C_8$ alkenyl, $C_2$–$C_6$ alkynyl, —(CH$_2$)$_m$(C$_6$–$C_{10}$ aryl), or —(CH$_2$)$_m$(5–10 membered heteroaryl), wherein m is an integer ranging from 0 to 4;

each $R^8$ is independently H, $C_1$–$C_{10}$ alkyl, $C_2$–$C_{10}$ alkenyl, $C_2$–$C_{10}$ alkynyl, —(CH$_2$)$_q$CR$^{11}$R$^{12}$(CH$_2$)$_r$NR$^{13}$R$^{14}$ wherein q and r are each independently an integer ranging from 0 to 3 except q and r are not both 0, —(CH$_2$)$_m$(C$_8$–$C_{10}$ aryl), or —(CH$_2$)$_m$(5–10 membered heteroaryl), wherein m is an integer ranging from 0 to 4, and wherein the foregoing $R^8$ groups, except H, are optionally substituted by 1 to 3 $R^{16}$ groups;

or where $R^8$ is as —CH$_2$NR$^8$R$^{15}$, $R^{15}$ and $R^8$ may be taken together to form a 4–10 membered monocydic or polycydic saturated ring or a 5–10 membered heteroaryl ring, wherein said saturated and heteroaryl rings optionally include 1 or 2 heteroatoms selected from O, S and —N(R$^8$)—, in addition to the nitrogen to which $R^{15}$ and $R^8$ are attached, said saturated ring optionally includes 1 or 2 carbon-carbon double or triple bonds, and said saturated and heteroaryl rings are optionally substituted by 1 to 3 $R^{16}$ groups;

each $R^9$ and $R^{10}$ is independently H or $C_1$–$C_8$ alkyl;

each $R^{11}$, $R^{12}$, $R^{13}$ and $R^{14}$ is independently selected from H, $C_1$–$C_{10}$ alkyl, —(CH$_2$)$_m$(C$_6$–$C_{10}$ aryl), aryl), and —CH$_2$)$_m$(5–10 membered heteroaryl), wherein m is an integer ranging from 0 to 4, and wherein the foregoing $R^{11}$, $R^{12}$, $R^{13}$ and $R^{14}$ groups, except H, are optionally substituted by 1 to 3 $R^{16}$ groups;

or $R^{11}$ and $R^{13}$ are taken together to form —(CH$_2$)$_p$— wherein p is an integer ranging from 0 to 3 such that a 4–7 membered saturated ring is formed that optionally includes 1 or 2 carbon-carbon double or triple bonds;

or $R^{13}$ and $R^{14}$ are taken together to form a 4–10 membered monocyclic or polycylic saturated ring or a 5–10 membered heteroaryl ring, wherein said saturated and heteroaryl rings optionally include 1 or 2 heteroatoms selected from O, S and —N(R$^8$)—, in addition to the nitrogen to which $R^{13}$ and $R^{14}$ are attached, said saturated ring optionally includes 1 or 2 carbon-carbon double or triple bonds, and said saturated and heteroaryl rings are optionally substituted by 1 to 3 $R^{16}$ groups;

$R^{15}$ is H, $C_1$–$C_{10}$ alkyl, $C_2$–$C_{10}$ alkenyl, or $C_2$–$C_{10}$ alkynyl, wherein the foregoing $R^{15}$ groups are optionally substituted by 1 to 3 substituents independently selected from halo and —$OR^9$;

each $R^{16}$ is independently selected from halo, cyano, nitro, trifluoromethyl, azido, —$C(O)R^{17}$, —$C(O)OR^{17}$, —$C(O)OR^{17}$, —$OC(O)OR^{17}$, —$NR^6C(O)R^7$, —$C(O)$ $NR^6R^7$, —$NR^6R^7$, hydroxy, $C_1$–$C_6$ alkyl, $C_1$–$C_6$ alkoxy, —$(CH_2)_m(C_6$–$C_{10}$ aryl), and —$(CH_2)_m$(5–10 membered heteroaryl), wherein m is an integer ranging from 0 to 4, and wherein said aryl and heteroaryl substituents are optionally substituted by 1 or 2 substituents independently selected from halo, cyano, nitro, trifluoromethyl, azido, —$C(O)R^{17}$, —$C(O)OR^{17}$, —$C(O)OR^{17}$, —$OC(O)OR^{17}$, —$NR^6C(O)R^7$, —$C(O)NR^6R^7$, —$NR^6R^7$, hydroxy, $C_1$–$C_6$ alkyl, and $C_1$–$C_6$ alkoxy;

each $R^{17}$ is independently selected from H, $C_1$–$C_{10}$ alkyl, $C_2$–$C_{10}$ alkenyl, $C_2$–$C_{10}$ alkynyl, —$(CH_2)_m(C_6$–$C_{10}$ aryl), and —$(CH_2)_m$(5–10 membered heteroaryl), wherein m is an integer ranging from 0 to 4;

with the proviso that $R^8$ is not H where $R^3$ is —$CH_2S(O)_mR^8$.

Preferred compounds of formula 1 include those wherein $R^1$ is hydroxy, $R^2$ is hydroxy, $R^3$ is —$CH_2NR^{15}R^8$ or —$CH_2SR^8$, and $R^4$ is H.

Other preferred compounds of formula 1 include those wherein $R^1$ is hydroxy, $R^2$ is hydroxy, $R^3$ is —$CH_2NR^8R^{15}$, $R^4$ is H, $R^{15}$ and $R^8$ are each selected from H, $C_1$–$C_{10}$ alkyl, $C_2$–$C_{10}$ alkenyl, and $C_2$–$C_{10}$ alkynyl, wherein said $R^{15}$ and $R^8$ groups, except H, are optionally substituted by 1 or 2 substituents independently selected from hydroxy, halo and $C_1$–$C_6$ alkoxy. Specific preferred compounds having the foregoing general structure include those wherein $R^{15}$ is either H or is selected from the following groups from which $R^8$ is also independently selected: methyl, ethyl, allyl, n-butyl, isobutyl, 2-methoxyethyl, cyclopentyl, 3-methoxypropyl, 3-ethoxypropyl, n-propyl, isopropyl, 2-hydroxyethyl, cyclopropyl, 2,2,2-trifluoroethyl, 2-propynyl, sec-butyl, tert-butyl, and n-hexyl.

Other preferred compounds of formula 1 include those wherein $R^1$ is hydroxy, $R^2$ is hydroxy, $R^3$ is —$CH_2NHR^8$, $R^4$ is H, and $R^8$ is —$(CH_2)_m(C_6$–$C_{10}$ aryl) wherein m is an integer ranging from 0 to 4. Specific preferred compounds having the foregoing general structure include those wherein $R^8$ is phenyl or benzyl.

Other preferred compounds of formula 1 include those wherein $R^1$ is hydroxy, $R^2$ is hydroxy, $R^3$ is —$CH_2NR^{15}R^8$, $R^4$ is H, and $R^{15}$ and $R^8$ are taken together to form a saturated ring. Specific preferred compounds having the foregoing general structure include those wherein $R^6$ and $R^8$ are taken together to form a piperidino, trimethyleneimino, or morpholino ring.

Other preferred compounds of formula 1 include those wherein $R^1$ is hydroxy, $R^2$ is hydroxy, $R^3$ is —$CH_2NR^{15}R^8$, $R^4$ is H, and $R^{15}$ and $R^8$ are taken together to form a heteroaryl ring optionally substituted by 1 or 2 $C_1$–$C_6$ alkyl groups. Specific preferred compounds having the foregoing general structure include those wherein $R^{15}$ and $R^8$ are taken together to form a pyrrolidino, triazolyl, or imidazolyl ring wherein said heteroaryl groups are optionally substituted by 1 or 2 methyl groups.

Other preferred compounds of formula 1 include those wherein $R^1$ is hydroxy, $R^2$ is hydroxy, $R^3$ is —$CH_2SR^8$, $R^4$ is H, and $R^8$ is selected from $C_1$–$C_{10}$ alkyl, $C_2$–$C_{10}$ alkenyl, and $C_2$–$C_{10}$ alkynyl, wherein said $R^8$ groups are optionally substituted by 1 or 2 substituents independently selected from hydroxy, halo and $C_1$–$C_6$ alkoxy. Specific preferred compounds having the foregoing general structure include those wherein $R^8$ is methyl, ethyl, or 2-hydroxyethyl.

Other preferred compounds of formula 1 include those wherein $R^1$ is hydroxy, $R^2$ is hydroxy, $R^4$ is H, and $R^3$ is selected from $C_1$–$C_{10}$ alkyl, $C_2$–$C_{10}$ alkenyl, and $C_2$–$C_{10}$ alkynyl, wherein said $R^3$ groups are optionally substituted by 1 or 2 substituents independently selected from hydroxy, —$C(O)R^{17}$, —$NR^6R^7$, halo, cyano, azido, 5-10 membered heteroaryl, and $C_1$–$C_6$ alkoxy. Specific preferred compounds having the foregoing general structure include those wherein $R^3$ is methyl, allyl, vinyl, ethynyl, 1-methyl-1-propenyl, 3-methoxy-1-propynyl, 3-dimethylamino-1-propynyl, 2-pyridylethynyl, 1-propynyl, 3-hydroxy-1-propynyl, 3-hydroxy-1-propenyl, 3-hydroxypropyl, 3-methoxy-1-propenyl, 3-methoxypropyl, 1-propynyl, n-butyl, ethyl, propyl, 2-hydroxyethyl, formylmethyl, 6-cyano-1-pentynyl, 3-dimethylamino-1-propenyl, or 3-dimethylaminopropyl.

Other preferred compounds of formula 1 include those wherein $R^1$ is hydroxy, $R^2$ is hydroxy, $R^4$ is H, and $R^3$ is —$(CH_2)_m$(5–10 membered heteroaryl) wherein m is an integer ranging from 0 to 4. Specific preferred compounds having the foregoing general structure include those wherein $R^3$ is 2-thienyl, 2-pyridyl, 1-methyl-2-imidazolyl, 2-furyl, or 1-methyl-2-pyrrolyl.

Other preferred compounds of formula 1 include those wherein $R^1$ is hydroxy, $R^2$ is hydroxy, $R^4$ is H, and $R^3$ is —$(CH_2)_m(C_6$–$C_{10}$ aryl) wherein m is an integer ranging from 0 to 4. Specific preferred compounds having the foregoing general structure include those wherein $R^3$ is phenyl.

Specific compounds of formula 1 include those wherein $R^2$ and $R^3$ are taken together to form an oxazolyl ring as shown below

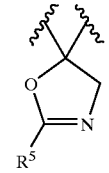

wherein $R^5$ is as defined above.

Specific compounds of formula 1 include those wherein $R^3$ is selected from the following:

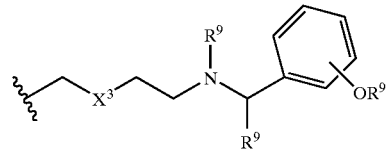

wherein $X^3$ is O, S or —$N(R^{15})$—, and wherein the —$OR^9$ group may be attached at any available carbon on the phenyl group.

The invention also relates to a pharmaceutical composition for the treatment of a bacterial infection or a protozoa infection in a mammal, fish, or bird which comprises a therapeutically effective amount of a compound of formula 1, or a pharmaceutically acceptable salt thereof, and a pharmaceutically acceptable carrier.

The invention also relates to a method of treating a bacterial infection or a protozoa infection in a mammal, fish, or bird which comprises administering to said mammal, fish or bird a therapeutically effective amount of a compound of formula 1 or a pharmaceutically acceptable salt thereof.

The term "treatment", as used herein, unless otherwise indicated, includes the treatment or prevention of a bacterial infection or protozoa infection as provided in the method of the present invention.

As used herein, unless otherwise indicated, the terms "bacterial infection(s)" and "protozoa infection(s)" include bacterial infections and protozoa infections that occur in mammals, fish and birds as well as disorders related to bacterial infections and protozoa infections that may be treated or prevented by administering antibiotics such as the compounds of the present invention. Such bacterial infections and protozoa infections, and disorders related to such infections, include the following: pneumonia, otitis media, sinusitus, bronchitis, tonsillitis, and mastolditis related to infection by *Streptococcus pneumoniae, Haemophilus influenzae, Moraxella catarrhalis, Staphylococcus aureus,* or *Peptostreptococcus*spp.; pharyngitis, rheumatic fever, and glomerulonephritis related to infection by *Streptococcus pyogenes,* Groups C and G streptococci, *Clostridium diptheriae,* or *Actinobacillus haemolyticum*; respiratory tract infections related to infection by *Mycoplasma pneumoniae, Legionella pneumophila, Streptococcus pneumoniae, Haemophilus influenzae,* or *Chlamydia pneumoniae*; uncomplicated skin and soft tissue infections, abscesses and osteomyelitis, and puerperal fever related to infection by *Staphylococcus aureus,* coagulase-positive staphylococci (i.e., *S. epidermidis, S. hemolyticus,* etc.), *Streptococcus pyogenes, Streptococcus agalactiae,* Streptococcal groups C–F (minute-colony streptococci), viridans streptococci, *Corynebacterium minutissimum, Clostridium*spp., or *Bartonella henselae*; uncomplicated acute urinary tract infections related to infection by *Staphylococcus saprophyticus* or *Enterococcus* spp.; urethritis and cervicitis; and sexually transmitted diseases related to infection by *Chlamydia trachomatis, Haemophilus ducreyl, Treponema pallidum, Ureaplasma urealyticum,* or *Neiserria gonorrheae*; toxin diseases related to infection by *S. aureus* (food poisoning and Toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae,* or *Listeria* spp.; disseminated *Mycobacterium avium* complex (MAC) disease related to infection by *Mycobacterium avium,* or *Mycobacterium intracellulare*; gastroenteritis related to infection by *Campylobacter jejuni*; intestinal protozoa related to infection by *Cryptosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis related to infection by *Helicobacter pylori* or *Chlamydia pneumoniae*. Bacterial infections and protozoa infections and disorders related to such infections that may be treated or prevented in animals include the following: bovine respiratory disease related to infection by *P. haem., P. multocida, Mycoplasma bovis,* or *Bordetella* spp.; cow enteric disease related to infection by *E. coli* or protozoa (i.e., coccidia, cryptosporidia, etc.); dairy cow mastitis related to infection by *Staph. aureus, Strep. uberis, Strep. agalactiae, Strep. dysgalactiae, Klebsiella* spp., *Corynebacterium,* or *Enterococcus* spp.; swine respiratory disease related to infection by *A. pleuro., P. multocida,* or *Mycoplasma* spp.; swine enteric disease related to infection by *E. coli, Lawsonia intracellularis, Salmonella,* or *Serpulina hyodyisinteriae*; cow footrot related to infection by *Fusobacterium* spp.; cow metritis related to infection by *E. coli*; cow hairy warts related to infection by *Fusobacterium necrophorum* or *Bacteroides nodosus*; cow pink-eye related to infection by *Moraxella bovis*; cow premature abortion related to infection by protozoa (i.e. neosporium); urinary tract infection in dogs and cats related to infection by *E. coli*; skin and soft tissue infections in dogs and cats related to infection by *Staph. epidermidis, Staph. intermedius, coagulase neg. Staph.* or *P. multocida*; and dental or mouth infections in dogs and cats related to infection by *Alcaligenes* spp., *Bacteroides* spp., *Clostridium* spp., *Enterobacter* spp., *Eubacterium, Peptostreptococcus, Porphyromonas,* or *Prevotella.* Other bacterial infections and protozoa infections and disorders related to such infections that may be treated or prevented in accord with the method of the present invention are referred to in J. P. Sanford et al., "The Sanford Guide To Antimicrobial Therapy," 26th Edition, (Antimicrobial Therapy, Inc., 1996).

The present invention also relates to a method of preparing the above compound of formula 1, or a pharmaceutically acceptable salt thereof, wherein $R^3$ is —$CH_2S(O)_mR^8$, —$CH_2OR^8$ or —$CH_2NR^8R^{15}$, wherein n, $R^{15}$ and $R^8$ are as defined above with the proviso that $R^8$ is not H where $R^3$ is —$CH_2S(O)_mR^8$, which comprises treating a compound of the formula

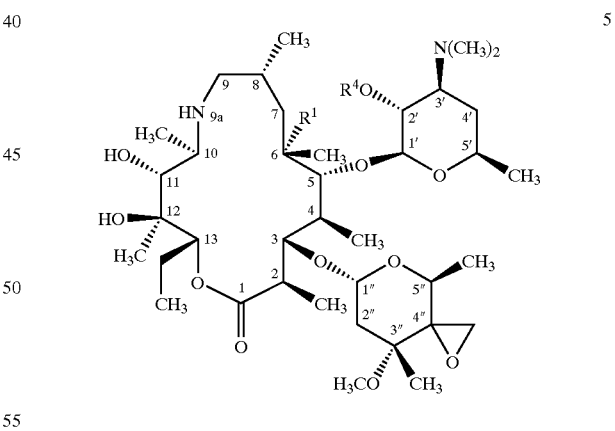

5 wherein $R^1$ and $R^4$ are as defined above, with a compound of the formula $HSR^8$, $HOR^8$ or $HNR^{15}R^8$, wherein n, $R^{15}$ and $R^8$ are as defined above, optionally followed by oxidation of the —$SR^8$ subsbtuent to form —$S(O)R^8$ or —$S(O)_2R^8$.

In a further aspect of the above process of preparing the compound of formula 1, or a pharmaceutically acceptable salt thereof, the above compound of formula 5 is prepared by treating a compound of the formula

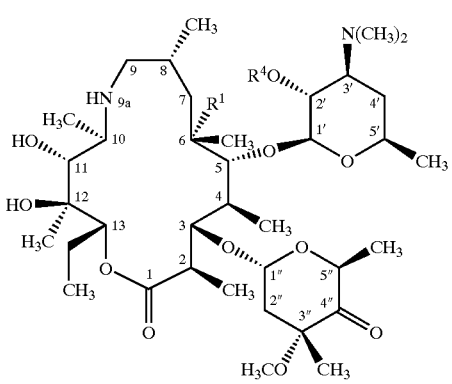

wherein R[1] and R[4] are as defined above, with (CH$_3$)$_3$S(O)$_n$X$^2$, wherein n is 0 or 1 and X$^2$ is halo, —BF$_4$ or —PF$_6$, preferably iodo or —BF$_4$, in the presence of a base such as potassium tert-butoxide, sodium tert-butoxide, sodium ethoxide, sodium hydride, 1,1,3,3-tetramethylguanidine, 1,8-diazabicyclo[5.4.0]undec-7-ene, 1,5-diazabicyclo[4.3.0]non-5-ene, potassium hexamethyldisillazide (KHMDS), potassium ethoxide, or sodium methoxide, preferably KHMDS or a sodium-containing base such as sodium hydride.

The present invention also relates to the above compounds of formulas 4 and 5 which, as indicated above, are useful in the preparation of the above compounds of formula 1 and pharmaceutically acceptable salts thereof.

The term "hydroxy protecting group", as used herein, unless otherwise indicated, includes acetyl, benzyloxycarbonyl, and various hydroxy protecting groups familiar to those skilled in the art include the groups referred to in T. W. Greene, P. G. M. Wuts, "Protective Groups In Organic Synthesis," (J. Wiley & Sons, 1991).

The term "halo", as used herein, unless otherwise indicated, includes fluoro, chloro, bromo or iodo.

The term "alkyl", as used herein, unless otherwise indicated, includes saturated monovalent hydrocarbon radicals having straight, cyclic or branched moieties, or mixtures thereof. It is to be understood that where cyclic moieties are Intended, at least three carbons in said alkyl must be present. Such cyclic moieties include cyclopropyl, cyclobutyl and cyclopentyl.

The term "alkoxy", as used herein, unless otherwise indicated, includes —O-alkyl groups wherein alkyl is as defined above.

The term "aryl", as used herein, unless otherwise indicated, includes an organic radical derived from an aromatic hydrocarbon by removal of one hydrogen, such as phenyl or naphthyl.

The term "5–10 membered heteroaryl", as used herein, unless otherwise indicated, includes aromatic heterocyclic groups containing one or more heteroatoms each selected from O, S and N, wherein each heterocyclic group has from 5 to 10 atoms in its ring system. Examples of suitable 5–10 membered heteroaryl groups include pyridinyl, imidazolyl, pyrimidinyl, pyrazolyl, (1,2,3,) and (1,2,4)-triazolyl, pyrazinyl, tetrazolyl, furyl, thienyl, isoxazolyl, oxazolyl, pyrrolyl and thiazolyl.

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of the present invention are those that form non-toxic acid addition salts, i.e., salts containing pharmacologically acceptable anions, such as the hydrochloride hydrobromide, hydroiodide, nitrate, sulfate, bisulfate, phosphate, acid phosphate, isonicotinate, acetate, lactate, salicylate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present invention that include an amino moiety may form pharmaceutically acceptable salts with various amino acids, in addition to the acids mentioned above.

Those compounds of the present invention that are acidic in nature are capable of forming base salts with various pharmacologically acceptable cations. Examples of such salts include the alkali metal or alkaline earth metal salts and, particularly, the calcium, magnesium, sodium and potassium salts of the compounds of the present invention.

Certain compounds of the present invention may have asymmetric centers and therefore exist in different enantiomeric and diastereomic forms. This invention relates to the use of all optical isomers and stereoisomers of the compounds of the present invention, and mixtures thereof, and to all pharmaceutical compositions and methods of treatment that may employ or contain them.

The present invention includes the compounds of the present invention, and the pharmaceutically acceptable salts thereof, wherein one or more hydrogen, carbon or other atoms are replaced by isotopes thereof. Such compounds may be useful as research and diagnostic tools in metabolism pharmacokinetic studies and in binding assays.

DETAILED DESCRIPTION OF THE INVENTION

The compounds of of the present invention may be prepared according to Schemes 1–3 below and the description that follows.

Scheme 1

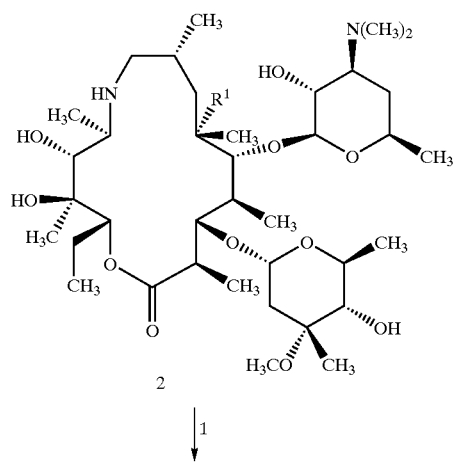

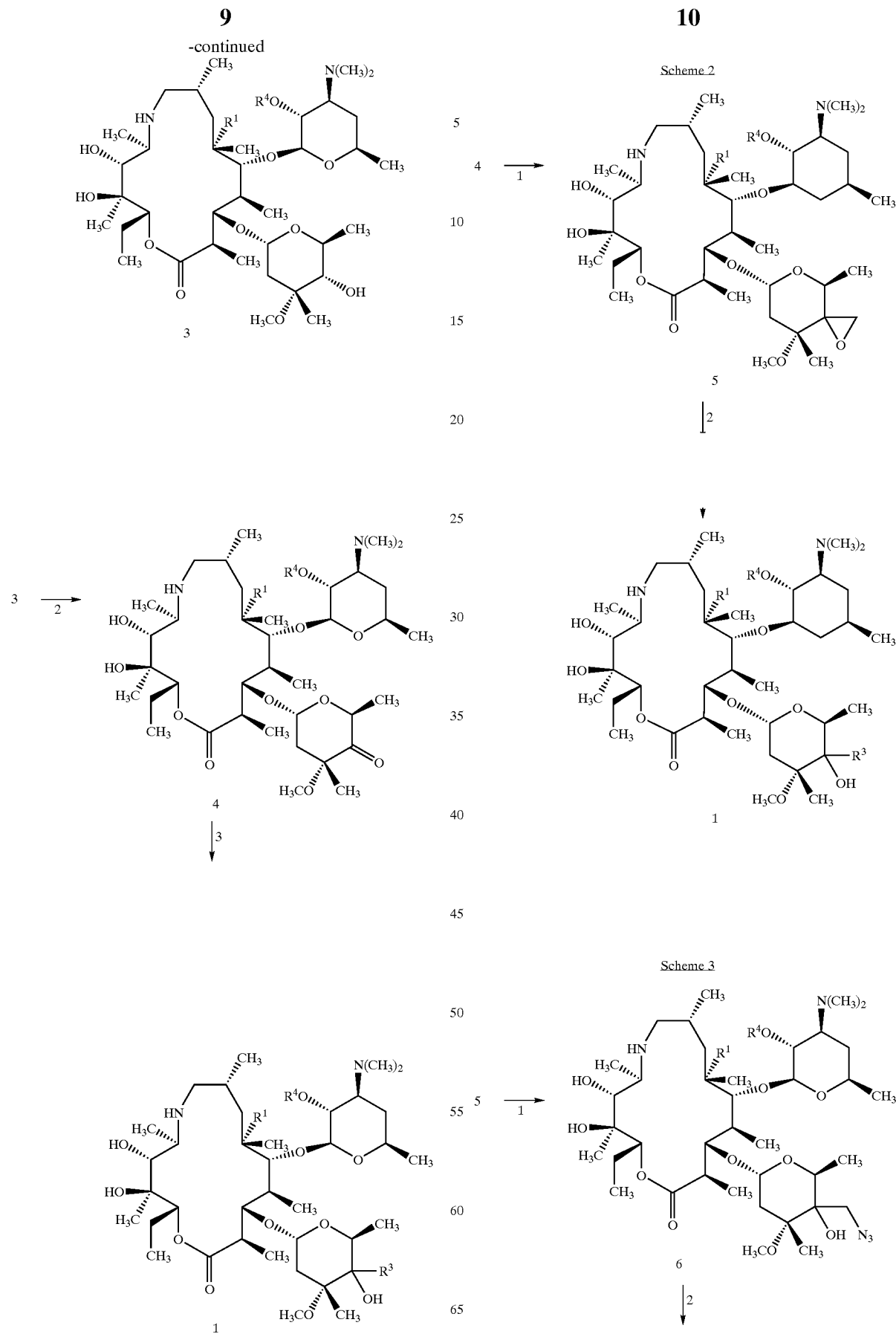

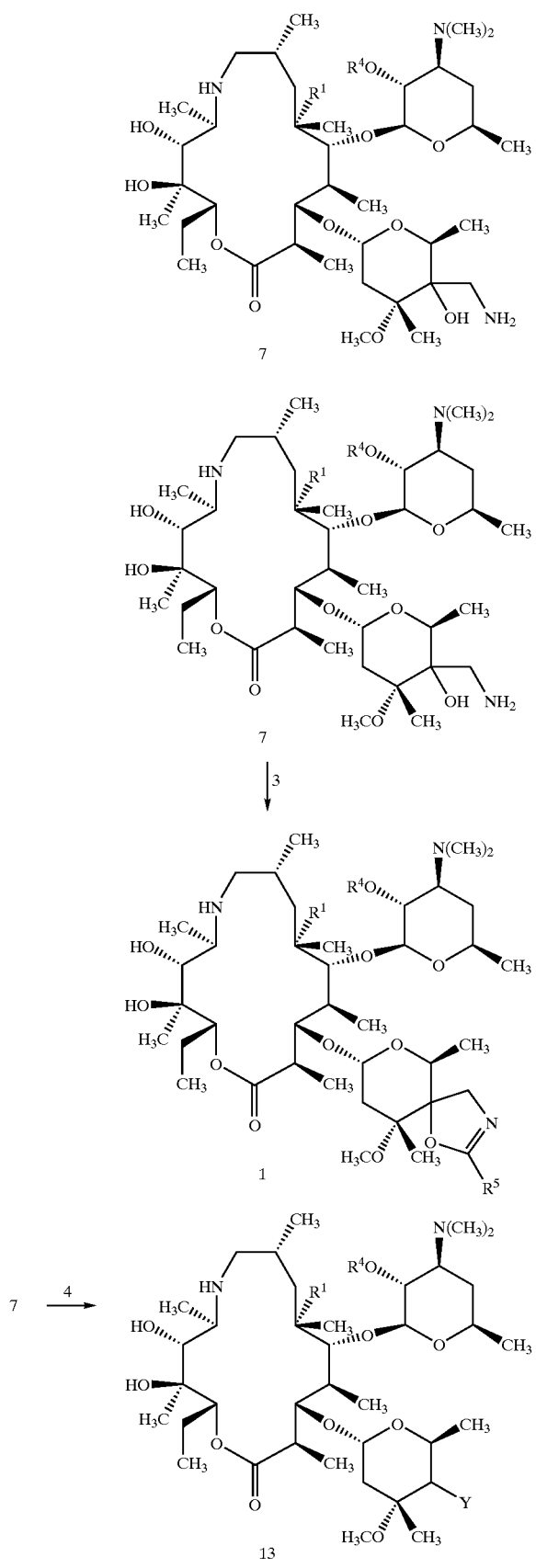

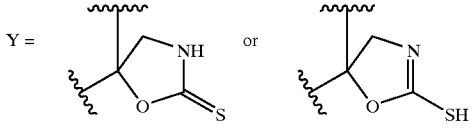

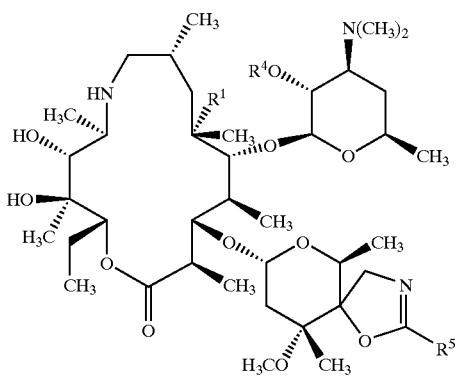

The compounds of the present invention are readily prepared. Referring to the Schemes illustrated above, the starting compound of formula 2 may be prepared according to one or more methods familiar to those skilled in the art including the synthetic methods described in U.S. Pat. Nos. 4,474,768 and 4,517,359, referred to above. In step 1 of Scheme 1, the C-2' hydroxy group may be selectively protected by treating the compound of formula 2 with one equivalent of acetic anhydride in dichloromethane in the absence of external base to provide the compound of formula 3 wherein $R^4$ is acetyl. The acetyl protecting group may be removed by treating the compound of formula 3 with methanol at 23–65° C. for 10–48 hours. The C-2' hydroxy may also be protected with other hydroxy protecting groups familiar to those skilled in the art, such as the benzyloxycarbonyl (Cbz) group. The C-9a amino group may also require protection before further synthetic modifications are performed. Suitable protecting groups for the amino moiety are Cbz and t-butyloxycarbonyl (Boc) groups. To protect the C-9a amino group, the macrolide may be treated with t-butyl dicarbonate in anhydrous tetrahydrofuran (THF) or benzyloxycarbonyl N-hydroxysuccinimide ester or benzylchloroformate to protect the amino group as its t-butyl or benzyl carbamate. Both the C-9a amino and C-2' hydroxy may be selectively protected with the Cbz group in one step by treating the compound of formula 2 with benzylchloroformate in THF and water. The Boc group may be removed by acid treatment and the Cbz group may be removed by conventional catalytic hydrogenation. In the following description, it is assumed that the C-9a amino moiety and the C-2' hydroxy group are protected and deprotected as would be deemed appropriate by those skilled in the art.

In step 2 of Scheme 1, the C-4' hydroxy group of the compound of formula 3 is oxidized to the corresponding ketone by methods familiar to those skilled in the art, including one or more methods described in the Journal of Antibiotics, 1988, pages 1029–1047. For example, the ketone of formula 4 may be prepared with DMSO and an appropriate activating agent. Typical reaction conditions for the oxidation include: (a) Moffatt oxidation which employs N-ethyl-N'(N,N-dimethylaminopropyl)carbodiimide and DMSO in the presence of pyridinium trifluoroacetate; or (b)

Swern oxidation in which oxalyl chloride and DMSO in $CH_2Cl_2$ is followed by the addition of triethylamine or alternatively trifluoroacetic anhydride and DMSO in $CH_2Cl_2$ is followed by the addition of triethylamine. In step 3 of Scheme 1, the compound of formula 4 is treated with $R^3MgX^1$ or $R^3$-Li and $Mg(X^1)_2$, wherein $X^1$ is a halide such as chloro or bromo, in a solvent such as THF, ethylene glycol dimethyl ether (DME), diisopropyl ether, toluene, diethyl ether, or tetramethylethylenediamine (TMEDA), hexanes, or a mixture of two or more of the foregoing solvents, preferably an ether solvent, at a temperature ranging from about $-78°$ C. to about room temperature (20–25° C.), to provide the compound of formula 1 wherein $R^2$ is hydroxy and $R^1$, $R^3$ and $R^4$ are as defined above.

Scheme 2 illustrates the preparation of compounds of formula 1 through use of an epoxide intermediate. In step 1 of Scheme 2, the compound of formula 5 may be generated by two methods. In one method (Method A), the compound of formula 4 is treated with $(CH_3)_3S(O)X^2$, wherein $X^2$ is halo, $-BF_4$ or $-PF_8$, preferably iodo, in the presence of a base such as potassium tert-butoxide, sodium tert-butoxide, sodium ethoxide, sodium hydride, 1,1,3,3-tetramethylguanidine, 1,8-diazabicyclo[5.4.0]undec-7-ene, 1,5-diazabicylo[4.3.0]non-5-ene, potassium ethoxide, or sodium methoxide, preferably a sodium-containing base such as sodium hydride, in a solvent such as THF, an ether solvent, dimethylformamide (DMF), or methyl sulfoxide (DMSO), or a mixture of two or more of the foregoing solvents, at a temperature within the range of about 0° C. to about 60° C., the compound of formula 5 is generated in which the following configuration of the epoxide moiety may predominate

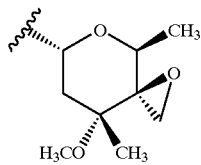

In a second method (Method B), the compound of formula 4 is treated with $(CH_3)_3SX^2$, wherein $X^2$ is halo, $-BF_4$ or $-PF_6$, preferably $-BF_4$, in the presence of a base such as as potassium tert-butoxide, sodium ethoxide, sodium tert-butoxide, sodium hydride, 1,1,3,3-tetramethylguanidine, 1,8-diazabicyclo[5.4.0]undec-7-ene, 1,5-diazabicylo[4.3.0] non-5-ene, potassium ethoxide, potassium hexamethyldisilazide (KHMDS) or sodium methoxide, preferably KHMDS, in a solvent such as THF, an ether solvent, DMF, or DMSO, or a mixture of two or more of the foregoing solvents, at a temperature within the range of about $-78°$ C. to about 60° C., to provide the compound of formula 5 in which the following configuration of the epoxide moiety predominates

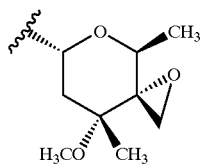

In step 2 of Scheme 2, the compound of formula 5 may be converted to a compound of formula 1 wherein $R^2$ is hydroxy and $R^3$ is a group that is attached to the C-4" carbon through a methylene group, such as where $R^3$ is $-CH_2NR^{15}R^8$ or $-CH_2S(O)_mR^8$ wherein n, $R^{15}$ and defined above. To prepare a compound of formula 1 wherein $R^3$ is $-CH_2NR^{15}R^8$, the compound of formula 5 may be treated with a compound of the formula $HNR^{15}R^8$, wherein $R^{15}$ and $R^8$ are as defined above, in the absence or presence of a polar solvent such as water, methanol, or THF, or a mixture of the foregoing solvents, at a temperature ranging from about room temperature to about 100° C., preferably about 60° C., optionally in the presence of a halide reagent such as potassium iodide, lithium perchlorate, magnesium perchlorate, lithium tetrafluoroborate, pyridinium hydrochloride, or a tetraalkylammonium halide reagent such as tetrabutylammonium iodide. To prepare a compound of formula 1 wherein $R^3$ is $-CH_2S(O)_mR^8$ wherein n and $R^8$ are as defined above, the compound of formula 5 may be treated with a compound of the formula $HSR^8$ in the presence of $K_2CO_3$, KI, or sodium methoxide, in an aromatic solvent such as methanol, benzene or toluene at a temperature ranging from about room temperature to about 120° C. As appropriate, the sulfur moiety may be oxidized to $-SO-$ or $-SO_2-$ according to methods familiar to those skilled in the art. To prepare a compound of formula 1 wherein $R^3$ is $-CH_2SR^8$ and $R^8$ is $-(CH_2)_qCR^{11}R^{12}(CH_2)_r$ $NR^{13}R^{14}$, wherein the substituents of said $R^8$ group are as defined above, the compound of formula 5 may be treated with a compound of the formula $HS-(CH_2)_q CR^{11}R^{12}(CH_2)_r$- NPhth, wherien NPhth represents phthalimido, and potassium iodide to provide the compound of formula 1 wherein $R^3$ is $-CH_2S(CH_2)_qCR^{11}R^{12}(CH_2)_r$ $NH_2$, after removal of the phthalimido moiety, which may be further modified as necessary. Using the same or an analogous method, a compound of formula 1 wherein $R^3$ is $-CH_2NR^{15}R^8$ and $R^8$ is $-(CH_2)_qCR^{11}R^{12}(CH_2)_rNR^{13}R^{14}$ may be prepared by treating the compound of formula 5 with either a compound of the formula $HNR^9-(CH_2)_qCR^{11}R^{12}$ $(CH_2)_r-NR^{13}R^{14}$ or a compound of the formula $H_2N-$ $(CH_2)_qCR^{11}R^{12}(CH_2)_r-NH_2$ followed by reductive alkylation of the nitrogen atoms. Using the same or an analogous method, a compound of formula 1 wherein $R^3$ is $-CH_2OR^8$ and $R^8$ is as defined above may be prepared by treating a compound of formula 5 with a compound of the formula $HOR^8$.

Scheme 3 illustrates the preparation of compounds of formula 1 in which $R^2$ and $R^3$ are taken together to form an oxazolyl moiety. In step 1 of Scheme 3, the compound of formula 5 is treated with sodium azide in the presence of $NH_4Cl$ in methanol or water, or a mixture of the two solvents, at a temperature ranging from about 0° C. to about 100° C., preferably about 80° C., to provide the compound of formula 6. In step 2 of Scheme 3, the compound of formula 6 may be converted to the corresponding amine of formula 7 via conventional catalytic hydrogenation. Preferably, such hydrogenation is done using Pd (10% on carbon) powder under an $H_2$ atmosphere (1 atm). The resulting amine of formula 7 may be converted to various compounds of formula 1 wherein $R^3$ is $-CH_2NR^{15}R^8$ using conventional synthetic methods such as reductive amination.

In step 3 of Scheme 3, the compound of formula 7 may be converted to the compound of formula 1 wherein $R^2$ and $R^3$ are taken together as shown by treating the compound of formula 7 with a compound of formula $R^5-CN$, $R^5-C=N$ $(OCH_3)$, $R^5-C=N(OC_2H_5)$, $R^5-C(O)Cl$, or $R^5-CO_2H$, wherein $R^5$ is as defined above, except it is not $NH_2$, in the presence or absence of an acid, such as HCl, or a Lewis acid, such as $ZnCl_2$ or $BF_4Et_3O$, or a base, such as NaOH or TEA, in a solvent such as THF, a chlorohydrocarbon (such as $CH_2Cl_2$ or chlorobenzene), at a temperature ranging from about room temperature to reflux. In the alternative, the compound of formula 7 may proceed as indicated in steps 4 and 5 of Scheme 3. In step 4 of Scheme 3, the compound of formula 7 is treated with thiocarbonyldiimidazole in methylene chloride at a temperature ranging from about 0° C. to room temperature to provide the compound of formula 13. In step 5 of Scheme 3, the compound of formula 13 is treated with $R^5$—$X^1$, wherein $X^1$ is a halide such as bromo or iodo, and a base such as sodium methoxide in a solvent such as methanol or acetone, or a mixture of the two solvents, at a temperature ranging from about 0° C. to room temperature.

The compounds of the present invention may have asymmetric carbon atoms and therefore exist in different enantiomeric and diastereomeric forms. Diastereomeric mixtures can be separated into their individual diastereomers on the basis of their physical chemical differences by methods known to those skilled in the art, for example, by chromatography or fractional crystallization. Enantiomers may be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. The use of all such isomers, including diastereomer mixtures and pure enantiomers, are considered to be part of the present invention.

The compounds of the present invention that are basic in nature are capable of forming a wide variety of different salts with various inorganic and organic acids. Although such salts must be pharmaceutically acceptable for administration to mammals, it is often desirable in practice to initially isolate the compound of the present invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired salt can also be precipitated from a solution of the free base in an organic solvent by adding to the solution an appropriate mineral or organic acid.

Those compounds of the present invention that are acidic in nature are capable of forming base salts with various cations. For compounds that are to be administered to mammals, fish or birds such salts must be pharmaceutically acceptable. Where a pharmaceutically acceptable salt is required, it may be desirable to initially isolate the compound of the present invention from the reaction mixture as a pharmaceutically unacceptable salt and then simply convert the latter to a pharmaceutically acceptable salt in a process analogous to that described above relating to the conversion of pharmaceutically unacceptable acid addition salts to pharmaceutically acceptable salts. Examples of base salts include the alkali metal or alkaline-earth metal salts and particularly the sodium, amine and potassium salts. These salts are all prepared by conventional techniques. The chemical bases which are used as reagents to prepare the pharmaceutically acceptable base salts of this invention are those which form non-toxic base salts with the acidic compounds of the present invention. Such non-toxic base salts include those derived from such pharmacologically acceptable cations as sodium, potassium, calcium, magnesium, various amine cations, etc. These salts can easily be prepared by treating the corresponding acidic compounds with an aqueous solution containing the desired pharmacologically acceptable bases with cations such as sodium, potassium, calcium, magnesium, various amine cations, etc., and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The antibacterial and antiprotozoa activity of the compounds of the present invention against bacterial and protozoa pathogens is demonstrated by the compound's ability to inhibit growth of defined strains of human (Assay I) or animal (Assays II and III) pathogens.

Assay I

Assay I, described below, employs conventional methodology and interpretation criteria and is designed to provide direction for chemical modifications that may lead to compounds that circumvent defined mechanisms of macrolide resistance. In Assay I, a panel of bacterial strains is assembled to include a variety of target pathogenic species, including representatives of macrolide resistance mechanisms that have been characterized. Use of this panel enables the chemical structure/activity relationship to be determined with respect to potency, spectrum of activity, and structural elements or modifications that may be necessary to obviate resistance mechanisms. Bacterial pathogens that comprise the screening panel are shown in the table below. In many cases, both the macrolide-susceptible parent strain and the macrolide-resistant strain derived from it are available to provide a more accurate assessment of the compound's ability to circumvent the resistance mechanism. Strains that contain the gene with the designation of ermA/ermB/ermC are resistant to macrolides, lincosamides, and streptogramin B antibiotics due to modifications (methylation) of 23S rRNA molecules by an Erm methylase, thereby generally prevent the binding of all three structural classes. Two types of macrolide efflux have been described; msrA encodes a component of an efflux system in staphylococci that prevents the entry of macrolides and streptogramins while mefA/E encodes a transmembrane protein that appears to efflux only macrolides. Inactivation of macrolide antibiotics can occur and can be mediated by either a phosphorylation of the 2'-hydroxyl (mph) or by cleavage of the macrocyclic lactone (esterase). The strains may be characterized using conventional polymerase chain reaction (PCR) technology and/or by sequencing the resistance determinant. The use of PCR technology in this application is described in J. Sutcliffe et al., "Detection Of Erythromycin-Resistant Determinants By PCR", *Antimicrobial Agents and Chemotherapy*, 40(11), 2562–2566 (1996). The assay is performed in microtiter trays and interpreted according to *Performance Standards for Antimicrobial Disk Susceptibility Tests—Sixth Edition: Approved Standard*, published by The National Committee for Clinical Laboratory Standards (NCCLS) guidelines; the minimum inhibitory concentration (MIC) is used to compare strains. Compounds are initially dissolved in dimethylsulfoxide (DMSO) as 40 mg/ml stock solutions.

| Strain Designation | Macrolide Resistance Mechanism(s) |
| --- | --- |
| Staphylococcus aureus 1116 | susceptible parent |
| Staphylococcus aureus 1117 | ermB |
| Staphylococcus aureus 0052 | susceptible parent |
| Staphylococcus aureus 1120 | ermC |
| Staphylococcus aureus 1032 | msrA, mph, esterase |
| Staphylococcus hemolyticus 1006 | msrA, mph |
| Streptococcus pyogenes 0203 | susceptible parent |
| Streptococcus pyogenes 1079 | ermB |
| Streptococcus pyogenes 1062 | susceptible parent |
| Streptococcus pyogenes 1061 | ermB |
| Streptococcus pyogenes 1064 | ermB |
| Streptococcus agalactiae 1024 | susceptible parent |
| Streptococcus agalactiae 1023 | ermB |
| Streptococcus pneumoniae 1016 | susceptible |
| Streptococcus pneumoniae 1046 | ermB |
| Streptococcus pneumoniae 1095 | ermB |
| Streptococcus pneumoniae 1175 | mefE |
| Streptococcus pneumoniae 0085 | susceptible |
| Haemophilus influenzae 0131 | susceptible |
| Moraxella catarrhalis 0040 | susceptible |
| Moraxella catarrhalis 1055 | erythromycin intermediate resistance |
| Escherichia coli 0266 | susceptible |

Assay II is utilized to test for activity against *Pasteurella multocida* and Assay III is utilized to test for activity against *Pasteurella haemolytica*.

Assay II

This assay is based on the liquid dilution method in microliter format. A single colony of *P. multocida* (strain 59A067) is inoculated into 5 ml of brain heart infusion (BHI) broth. The test compounds are prepared by solubilizing 1 mg of the compound in 125 $\mu$l of dimethylsulfoxide (DMSO). Dilutions of the test compound are prepared using uninoculated BHI broth. The concentrations of the test compound used range from 200 $\mu$g/ml to 0.098 $\mu$g/ml by two-fold serial dilutions. The *P. multocida* inoculated BHI is diluted with uninoculated BHI broth to make a $10^4$ cell suspension per 200 $\mu$l. The BHI cell suspensions are mixed with respective serial dilutions of the test compound, and incubated at 37° C. for 18 hours. The minimum inhibitory concentration (MIC) is equal to the concentration of the compound exhibiting 100% inhibition of growth of *P. multocida* as determined by comparison with an uninoculated control.

Assay III

This assay is based on the agar dilution method using a Steers Replicator. Two to five colonies isolated from an agar plate are inoculated into BHI broth and incubated overnight at 37° C. with shaking (200 rpm). The next morning, 300 $\mu$l of the fully grown *P. haemolytica* preculture is inoculated into 3 ml of fresh BHI broth and is incubated at 37° C. with shaking (200 rpm). The appropriate amounts of the test compounds are dissolved in ethanol and a series of two-fold serial dilutions are prepared. Two ml of the respective serial dilution is mixed with 18 ml of molten BHI agar and solidified. When the inoculated *P. haemolytica* culture reaches 0.5 McFarland standard density, about 5 $\mu$l of the *P. haemolytica* culture is inoculated onto BHI agar plates containing the various concentrations of the test compound using a Steers Replicator and incubated for 18 hours at 37° C. Initial concentrations of the test compound range from 100–200 $\mu$g/ml. The MIC is equal to the concentration of the test compound exhibiting 100% inhibition of growth of *P. haemolytica* as determined by comparison with an uninoculated control.

The in vivo activity of the compounds of formula (I) can be determined by conventional animal protection studies well known to those skilled in the art, usually carried out in mice.

Mice are allotted to cages (10 per cage) upon their arrival, and allowed to acclimate for a minimum of 48 hours before being used. Animals are inoculated with 0.5 ml of a $3 \times 10^3$ CFU/ml bacterial suspension (*P. multocida* strain 59A006) intraperitoneally. Each experiment has at least 3 non-medicated control groups including one infected with 0.1× challenge dose and two infected with 1× challenge dose; a 10×challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or oral doses. Subcutaneous doses are administered into the loose skin in the back of the neck whereas oral doses are given by means of a feeding needle. In both cases, a volume of 0.2 ml is used per mouse. Compounds are administered 30 minutes, 4 hours, and 24 hours after challenge. A control compound of known efficacy administered by the same route is included in each test. Animals are observed daily, and the number of survivors in each group is recorded. The *P. multocida* model monitoring continues for 96 hours (four days) post challenge.

The $PD_{50}$ is a calculated dose at which the compound tested protects 50% of a group of mice from mortality due to the bacterial infecton which would be lethal in the absence of drug treatment.

The compounds of formula 1, and the pharmaceutically acceptable salts thereof (hereinafter "the active compounds"), may be adminstered through oral, parenteral, topical, or rectal routes in the treatment of bacterial and protozoa infections. In general, these compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and conditon of the subject being treated and the particular route of administration chosen. However, a dosage level that is in the range of about 4 mg/kg/day to about 50 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques will known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be adminstered in the form of liposome delivery systems, such as small unilamellar vesicles, large unllamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl-residues. Furthemnore, the active compounds may be coupled to a class of biodegradable polymers useful in achieving controlled release of a drug, for example, polytactic acid, polyglycolic acid, copolymers of polytactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The following Examples further illustrate the method and intermediates of the present invention. It is to be understood that the present invention is not limited to the specific details of the Examples provided below.

TABLE 1

The compounds of Examples 1–32 have the general formula 8 below with the R substituents indicated in the table below. The compounds were prepared as described in Preparations 1–7 below. In the table, the yield and mass spectra ("Mass Spec") data apply to the final product.

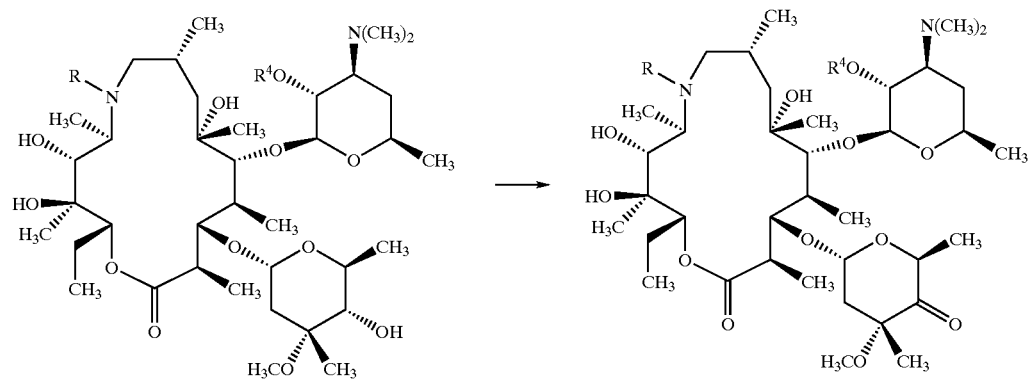

TABLE 1-continued

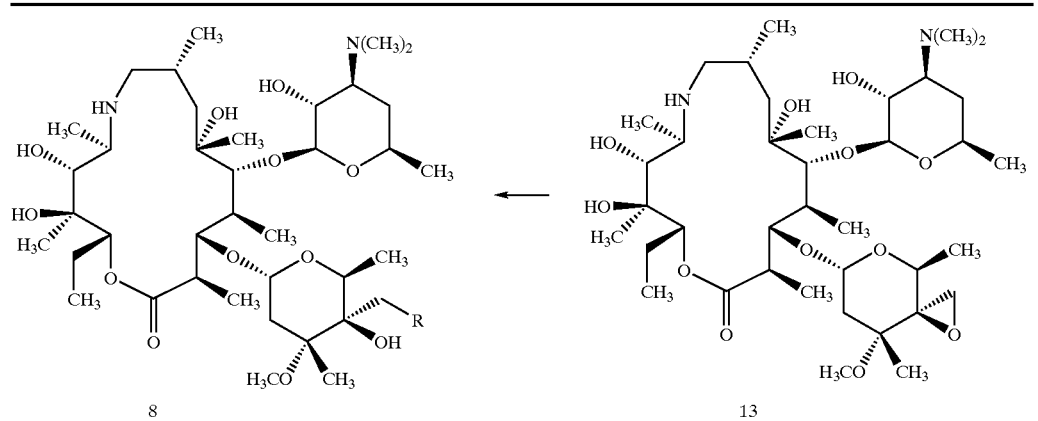

| Example | R Substituent | Preparation | Yield | Mass Spec |
|---|---|---|---|---|
| 1 | n-butylamino | 1 | 48% | 820 |
| 2 | 2-methoxyethylamino | 1 | 52% | 822 |
| 3 | piperidino | 1 | 61% | 832 |
| 4 | morpholino | 1 | 39% | 834 |
| 5 | t-butylamino | 1 | 23% | 821 |
| 6 | benzylamino | 1 | 34% | 854 |
| 7 | cyclopentylamino | 2 | 23% | 832 |
| 8 | propylamino | 2 | 11% | 806 |
| 9 | anilino | 1 | 21% | 841 |
| 10 | 2-methoxypropylamino | 1 | 46% | 835 |
| 11 | azido | 3 | 46% | 790 |
| 12 | hexylamino | 1 | 56% | 847 |
| 13 | 3-ethoxypropylamino | 1 | 52% | 851 |
| 14 | diethylamino | 2 | 53% | 821 |
| 15 | N-methylbutylamino | 1 | 76% | 835 |
| 16 | N-methylpropylamino | 2 | 59% | 819 |
| 17 | ethylamino | 5 | 18% | 792 |
| 18 | cyclopropylamino | 2 | 50% | 804 |
| 19 | ethylmethylamino | 2 | 92% | 806 |
| 20 | 2,2,2-trifluoroethylamino | 2 | 67% | 846 |
| 21 | allylamino | 1 | 59% | 804 |
| 22 | 2-hydroxyethylthio | 6 | 44% | 826 |
| 23 | dimethylamino | 1 | 71% | 793 |
| 24 | imidazol-1-yl | 4 | 42% | 815 |
| 25 | bis(2-hydroxyethyl)amino | 7 | 21% | 853 |
| 26 | pyrrolidino | 2 | 40% | 818 |
| 27 | 2-hydroxy-ethylmethylamino | 2 | 23% | 822 |
| 28 | 1,2,3-triazol-1-yl | 4 | 69% | 817 |
| 29 | 2-propynylamino | 2 | 51% | 802 |
| 30 | 2-methylimidazol-1-yl | 4 | 14% | 829 |
| 31 | diallylamino | 2 | 29% | 844 |
| 32 | 1,2,4-triazol-1-yt | 4 | 34% | 816 |

Preparation Methods for Table 1

With reference to the Scheme illustrated above, the compound of formula 11 wherein R is H and $R^4$ is H (25 g (34.01 mmol, 1.0 equiv)) was mixed in a solution with phenol red in 250 mL THF and 125 mL water. To this pink solution was slowly added 29 mL (204.1 mmol, 6.0 equiv) benzylchloroformate and 2N NaOH to keep the solution basic. The reaction was allowed to stir at room temperature overnight. The reaction mixture was concentrated to remove the THF and the aqueous phase was adjusted to the pH of 9.5 and extracted 3×500 mL EtOAc. The combined organic layers were washed with 500 mL brine and then dried over $Na_2CO_3$. Filtration, concentration of the filtrate, and drying afforded a crude material. Further purification was done by column chromatography (100% $CH_2Cl_2$ to remove impurities and then 5% MeOH/$CH_2Cl_2$ to remove product) to yield 32.6 g (96%) of a yellowish solid which was the compound of formula 11 wherein R and $R^4$ were both Cbz (MS (FAB) m/z 1003). 32.6 g (32.49 mmol, 1.0 equiv) of this product was dissolved in 216.6 mL $CH_2Cl_2$ and 27.3 mL of DMSO. To this solution, 21.2 g (110.5 mmol, 3.4 equiv) of EDC and 24.1 g (124.8 mmol, 3.8 equiv) PTFA were added. After stirring overnight the reaction was quenched with 150 mL of water and the pH was adjusted to 9.5 with the addition of 2N NaOH. The organic layer was extracted 3×150 mL $CH_2Cl_2$ and dried over $Na_2SO_4$. Filtration, concentration of the filtrate, and drying afforded a crude yellow oil. Further purification on a silica gel column (2% MeOHA/$CHCL_3$) to give 25.6 g (79%) of a yellowish solid which was the compound of formula 12 wherein both R and $R^4$ were Cbz.

14 g (13.98 mmol, 1.0 equiv) of the compound of formula 12 prepared as described above was dissolved in 1 L of 2-propanol and to this was added 14 g of 10% Pd/C. The mixture was hydrogenated at 50 psi for three days. 14 G of 10% Pd/C was added to the reaction and allowed to stir for another day. This was repeated again and stirred for another day. The catalyst was removed by filtration through Celite and a minimal wash of 2-propanol to yield 4.8 g (47%) of the compound of formula 12 wherein both R and $R^4$ were H (MS (APCi) m/z 734).

6.7 g (169.17 mmol, 6.2 equiv) of NaH (60% in oil dispersion) was washed twice with 150 mL hexanes to remove the mineral oil. The solid was diluted in 335 mL of DMSO and 38.4 g (174.62 mmol, 6.4 equiv) of $ME_3SOI$ was added in three portions. The soution was stirred for an hour or until it turned clear. 20 g (27.29 mmol, 1.0 equiv) of the compound of formula 12 wherein both R and $R^4$ were H was dissolved in 200 mL of THF. The ketone was transferred via cannula to the reaction flask and allowed to stir for 20 minutes. The reaction was quenched with 500 mL saturated $NaHCO_3$, extracted 4×500 mL EtOAc, and dried over $Na_2SO_4$. Filtration, concentration of the filtrate, and drying gave the crude oil. Further purification on 750 g of silica gel (5% $MeOH/CHCl_3$, 0.3% $NH_4OH$) afforded 8.8 g (43%) of a white solid which was the compound of formula 13 (MS (TS) m/z 747).

Preparation 1

250–500 mg of the above compound of formula 13 was dissolved in 1–2 mL of an amine corresponding to the R substituent specified in Table 1. A catalytic amount (20 mg) of pyridinium hydrochloride was added and the solution was heated to 50–85° C. for one to seven days. The reaction was worked up by quenching with 50 mL saturated $NaHCO_3$, extracted with 3×50 mL $CH_2Cl_2$, and dried over $Na_2SO_4$. Filtration, concentration of the filtrate, and drying gave a crude oil or solid. Further purification on a silica gel column (2–4% $MeOH/CHCl_3$, 0.2% $NH_4OH$) afforded the final product.

Preparation 2

250–500 mg of the above compound of formula 13 was dissolved in 1–2 mL of an amine corresponding to the R substituent specified in Table 1 in a sealed tube. A catalytic amount (20 mg) of pyridinium hydrochloride was added and the solution was heated to 50–75° C. for one to five days. The reaction was worked up by quenching with 50 mL saturated $NaHCO_3$, extracted with 3×50 mL $CH_2Cl_2$, and dried over $Na_2SO_4$. Filtration, concentration of the filtrate, and drying gave a crude oil or solid. Further purification on a silica gel column (2–4% $MeOH/CHCl_3$, 0.2% $NH_4OH$) afforded the final product.

Preparation 3

100 mg of the above compound of formula 13 was dissolved in $MeOH/H_2O$ (8:1). Sodium azide (7 equiv) and ammonium chloride (5.5 equiv) were added and the solution was heated to 60° C. for two days. The reaction was worked up by quenching with 50 mL saturated $NaHCO_3$, extracted with 3×50 mL $CH_2Cl_2$, and dried over $Na_2SO_4$. Filtration, concentration of the filtrate, and drying gave a crude oil or solid. Further purification on a silica gel column (2% $MeOH/CHCl_3$, 0.2% $NH_4OH$) afforded the final product.

Preparation 4

150–250 mg of the above compound of formula 13 was dissolved in 1–2 mL $MeOH/H_2O$ or MeOH. To this was added the heteroaromatic reagent corresponding to the R substituent specified in Table 1 (10–50 equiv) and a catalytic amount (20 mg) of pyridinium hydrochloride. The reaction mixture was heated at 45–50° C. for one to three days. The reaction was then quenched with 100 mL saturated $NaHCO_3$, extracted with 3×25 mL $CH_2Cl_2$, dried over $Na_2SO_4$, filtered, and concentrated to a solid. The solid was re-dissolved in 100 mL EtOAc and washed with 3×25 mL 2N NaOH to remove the excess reagent. Further purification on a silica gel column (2–5% $MeOH/CHCl_3$, 0.2% $NH_4OH$) afforded the final product.

Preparation 5

50 mg of the above compound of formula 13 was dissolved in 1 mL of an amine corresponding to the R substituent specified in Table 1. A small scoop of neutral alumina was added and the mixture was stirred at room temperature for seven days. The reaction was worked up by filtering through Celite™ (diatomaceous earth) and concentrated to a crude solid. Further purification on a silica gel column (5% $MeOH/CHCl_3$, 0.2% $NH_4OH$) afforded the final product.

Preparation 6

270 mg of the above compound of formula 13 was dissolved in 4 mL benzene. To this was added excess $K_2CO_3$ and 0.5 mL of thiol. The mixture stirred at room temperature for 16 hours. The reaction was quenched with 100 mL saturated $NaHCO_3$, extracted with 3×25 mL $CH_2Cl_2$, dried over $Na_2SO_4$, filtered, and concentrated to a solid. Further purifcation on a silica gel column (2%$MeOH/CHCl_3$, 0.2% $NH_4OH$) afforded the final product.

Preparation 7

250 mg of the above compound of formula 13 was dissolved in 0.5 mL bis(2-hydroxyethyl)amine and 2 mL 2-propanol in a sealed tube. A catalytic amount (20 mg) of pyridinium hydrochloride was added and the solution was heated to 75° C. for seven days. The reaction was worked up by quenching with 50 mL saturated $NaHCO_3$, extracted with 3×50 mL $CH_2Cl_2$ and dried over $Na_2SO_4$. Filtration, concentration of the filtrate, and drying gave a crude oil or solid. Further purification on a silica gel column (2% MeOH/$CHCl_3$, 0.2% $NH_4OH$) afforded the final product.

Examples 33–68 below describe the preparation of compounds having the general structure of formula 9 below wherein R is as defined in the examples.

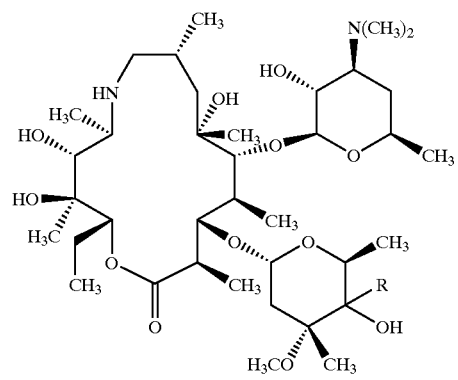

9

EXAMPLE 33

To a solution of the compound of formula 4 wherein $R^4$ is H (0.059 g, 0.08 mmol) in THF (2 mL) at 0° C. was added allylmagnesium bromide in $Et_2O$ (1.0 M, 0.5 mL). After 2 hours at 0° C., stirring was continued at room temperature for 12 hours. The reaction was diluted with a saturated aqueous solution of sodium bicarbonate (10 mL) and EtOAc (20 mL). After separation, the aqueous layer was washed with EtOAc (2×15 mL). The combined organic extracts were washed with a saturated aqueous solution of sodium bicarbonate (20 mL) and brine (25 mL), dried over $Na_2SO_4$ and concentrated under vacuum. Silica gel chromatography with $MeOH:CH_2Cl_2:NH_4OH$ (6:93:1 to 10:89:1) afforded 0.011 g (18% yield) of the compound of formula 9 wherein R is allyl: MS: 776 (TS).

EXAMPLE 34

To a solution of the compound of formula 4 wherein $R^4$ is H (0.059 g, 0.08 mmol) in DME (3 mL) at 0° C. was added vinylmagnesium bromide in THF (1.0 M, 0.56 mL). After stirring at 0° C. for 1 hour and at room temperature for 1 hour, the reaction mixture was diluted with a saturated aqueous solution of sodium bicarbonate (10 mL) and EtOAc (10 mL). After separation, the aqueous layer was washed with EtOAc (3×10 mL). The combined organic extracts were washed with a saturated aqueous solution of sodium bicarbonate (15 mL) and brine (20 mL), dried over $Na_2SO_4$ and concentrated under vacuum. Silica gel chromatography with $MeOH:CH_2Cl_2:NH_4OH$ (6:93:1) afforded 0.016 g (26% yield) of the compound of formula 9 wherein R is vinyl: MS: 762 (FAB).

EXAMPLE 35

To a flask containing $MgCl_2$ (0.095 g, 1 mmol) and DME (1 mL) at 0° C. was added 2-thienyl lithium (1.0 M, 1.0 mL). After 0.5 hour, a solution of the compound of formula 4 wherein $R^4$ is H (0.073 g, 0.1 mmol) in DME (2 mL) was introduced and stirring was continued at 0° C. for 1 hour, then at room temperature for 0.5 hour. The reaction mixture was diluted with a saturated aqueous solution of sodium bicarbonate (10 mL) and EtOAc (15 mL). After separation, the aqueous layer was washed with EtOAc (3×10 mL). The combined organic extracts were washed with a saturated aqueous solution of sodium bicarbonate (15 mL) and brine (20 mL), dried over $Na_2SO_4$ and concentrated under vacuum. Silica gel chromatography with $MeOH:CH_2Cl_2:NH_4OH$ (6:93:1) afforded 0.012 g (15% yield) of the compound of formula 9 wherein R is 2-thienyl: MS: 817 (TS).

EXAMPLE 36

To a solution of the compound of formula 4 wherein $R^4$ is H (0.147 g, 0.2 mmol) in DME (10 mL) at 0° C. was added ethynylmagnesium bromide in THF (0.5 M, 2.8 mL). After stirring at 0° C. for 1 hour and at room temperature for 1 hour, the reaction mixture was diluted with water (20 mL) and EtOAc (35 mL). After separation, the aqueous layer was washed with EtOAc (3×25 mL). The combined organic extracts were washed with a saturated aqueous solution of sodium bicarbonate (30 mL) and brine (30 mL), dried over $Na_2SO_4$ and concentrated under vacuum. Silica gel chromatography with $MeOH:CH_2Cl_2:NH_4OH$ (6:93:1 to 10:89:1) afforded 0.068 g (45% yield) of the compound of formula 9 wherein R is ethynyl: MS: 759 (API).

EXAMPLE 37

To a solution of the compound of formula 4 wherein $R^4$ is H (0.220 g, 0.3 mmol) in DME (15 mL) at 0° C. was added 1-methyl-1-propenylmagnesium bromide in THF (0.5 M, 42 mL). After stirring at room temperature for 3 hours, the reaction mixture was diluted with a saturated aqueous solution of sodium bicarbonate (20 mL) and EtOAc (30 mL). After separation, the aqueous layer was washed with EtOAc (3×10 mL). The combined organic extracts were washed with a saturated aqueous solution of sodium bicarbonate (25 mL) and brine (30 mL), dried over $Na_2SO_4$ and concentrated under vacuum. Silica gel chromatography with $MeOH:CH_2Cl_2:NH_4OH$ (6:93:1 to 10:89:1) afforded 0.068 g (26% yield) of the compound of formula 9 wherein R is 1-methyl-1-propenyl: MS: 790 (API).

EXAMPLE 38

To a solution of butylmagnesium bromide in THF (2.0 M, 1.0 mL) at 0° C. was added a solution of methyl propargyl ether (0.154 g, 0.2 mmol) in DME (3 mL). After stirring at 0° C. for 0.5 hour, a solution of the compound of formula 4 wherein $R^4$ is H (0.147 g, 0.2 mmol) in DME (7 mL) was added. After stirring at 0° C. for 0.5 hour and room temperature for 4 hours, the reaction mixture was diluted with water (20 mL) and EtOAc (25 mL). After separation, the aqueous layer was washed with EtOAc (3×20 mL). The combined organic extracts were washed with a saturated aqueous solution of sodium bicarbonate (20 mL) and brine (25 mL), dried over $Na_2SO_4$ and concentrated under vacuum. Silica gel chromatography with $MeOH:CH_2Cl_2:NH_4OH$ (6:93:1 to 10:89:1) afforded 0.081 g (50% yield) of the compound of formula 9 wherein R is 3-methoxy-1-propynyl: MS: 803 (API).

EXAMPLE 39

To a solution of methylmagnesium bromide in $Et_2O$ (3.0 M, 1.8 mL) at 0° C. was added a solution of 1-dimethylamino-2-propyne (0.154 g, 0.2 mmol) in THF (5 mL). After stirring at 0° C. for 6 hours, a solution of the compound of formula 4 wherein $R^{13}$ is H (0.147 g, 0.2 mmol) in DME (10 mL) was added at room temperature. After stirring at room temperature for 3 hours, the reaction mixture was diluted with water (40 mL) and EtOAc (50 mL). After separation, the aqueous layer was washed with EtOAc (3×50 mL). The combined organic extracts were washed with a saturated aqueous solution of sodium bicarbonate (40 mL) and brine (50 mL), dried over $Na_2SO_4$ and concentrated under vacuum. Silica gel chromatography with $MeOH:CH_2Cl_2:NH_4OH$ (6:93:1 to 8:91:1) afforded 0.140 g (57% yield) of the compound of formula 9 wherein R is 3-dimethylamino-1-propynyl: MS: 817 (API).

EXAMPLE 40

To a solution of methylmagnesium bromide in $Et_2O$ (3.0 M, 1.8 mL) and DME (1 mL) at 0° C. was added a solution of 2-ethynylpyridine (0.186 g, 1.8 mmol) in DME (2 mL). After stirring at 0° C. for 1 hour and room temperature for 1 hour, a solution of the compound of formula 4 wherein $R^4$ is H (0.110 g, 0.15 mmol) in DME (7 mL) was added at room temperature. After stirring at room temperature for 3 hours, the reaction mixture was diluted with water (20 mL) and EtOAc (40 mL). After separation, the aqueous layer was washed with EtOAc (3×30 mL). The combined organic extracts were washed with a saturated aqueous solution of sodium bicarbonate (50 mL) and brine (50 mL), dried over $Na_2SO_4$ and concentrated under vacuum. Silica gel chromatography with $MeOH:CH_2Cl_2:NH_4OH$ (6:93:1 to 10:89:1) afforded 0.066 g (53% yield) of the compound of formula 9 wherein R is 2-pyridylethynyl: MS: 836 (API).

EXAMPLE 41

To a round bottomed flask containing $MgBr_2$ (0.552 g, 3.0 mmol) and propynyl lithium (0.069 g, 1.5 mmol) at 0° C.

was added THF (5 mL). After 4 hours, a solution of the compound of formula 4 wherein $R^4$ is H (0.110 g, 0.15 mmol) in DME (10 mL) was introduced at room temperature and stirring was continued for 3 hours. The reaction mixture was diluted with water (30 mL) and EtOAc (30 mL). After separation, the aqueous layer was washed with EtOAc (3×40 mL). The combined organic extracts were washed with a saturated aqueous solution of sodium bicarbonate (50 mL) and brine (50 mL), dried over $Na_2SO_4$ and concentrated under vacuum. Silica gel chromatography with $MeOH:CH_2Cl_2:NH_4OH$ (6:93:1 to 7:92:1) afforded 0.060 g (52% yield) of the compound of formula 9 wherein R is 1-propynyl: MS: 817 (TS).

EXAMPLE 42

To a solution of methylmagnesium bromide in $Et_2O$ (3.0 M, 0.6 mL) mL) at 0° C. was added a solution of propargyl alcohol (0.346 mL, 0.289 g, 2.25 mmol) in THF (5 mL). After stirring at 0° C. for 3 hours, a solution of the compound of formula 4 wherein $R^4$ is H (0.110 g, 0.15 mmol) in DME (10 mL) was added at room temperature. After stirring at room temperature for 2 hours, the reaction mixture was diluted with water (35 mL) and EtOAc (50 mL). After separation, the aqueous layer was washed with EtOAc (3×40 mL). The combined organic extracts were washed with a saturated aqueous solution of sodium bicarbonate (50 mL) and brine (50 mL), dried over $Na_2SO_4$ and concentrated under vacuum. Silica gel chromatography with $MeOH:CH_2Cl_2:NH_4OH$ (6:93:1 to 15:84:1) afforded 0.038 (32% yield) of the compound of formula 9 wherein R is 3-hydroxy-1-propynyl: MS: 790 (API).

EXAMPLE 43

Palladium catalyst (20 mg, 10% Pd/C) was added to a solution of the compound from example 42 in isopropanol (8 mL). The reaction vessel was flushed and filled with hydrogen (50 psi) and shaken at room temperature for 24 hours. Filtration of an aliquot of the reaction mixture through Celite™ and concentration under vacuum afforded the compound of formula 9 wherein R is 3-hydroxy-1-propenyl: MS: 791 (API).

EXAMPLE 44

Palladium catalyst (20 mg, 10% Pd/C) was added to the remaining solution from example 43 and the reaction vessel was flushed and filled with hydrogen (50 psi) and shaken at room temperature for 48 hours. The reaction mixture was filtered through Celite™ and concentrated under vacuum. Silica gel chromatography with $MeOH:CH_2Cl_2:NH_4OH$ (6:93:1 to 8:91:1) afforded 0.018 g (57% yield) of the compound of formula 9 wherein R is 3-hydroxypropyl: MS: 793 (API)

EXAMPLE 45

Palladium catalyst (15 mg, 10% Pd/C) was added to a solution of the title compound from example 38 In isopropanol (8 mL). The reaction vessel was flushed and filled with hydrogen (50 psi) and shaken at room temperature for 24 hours. Filtration of an aliquot of the reaction mixture through Celite™ and concentration under vacuum afforded the compound of formula 9 wherein R is 3-methoxy-1-propenyl: MS: 806 (API).

EXAMPLE 46

Palladium catalyst (15 mg, 10% Pd/C) was added to the remaining solution from example 45 and the reaction vessel was flushed and filled with hydrogen (50 psi) and shaken at room temperature for 48 hours. The reaction mixture was filtered through Celite™ and concentrated under vacuum. Silica gel chromatography with $MeOH:CH_2Cl_2:NH_4OH$ (6:93:1 to 7:92:1) afforded 0.017 g (73% yield) of the compound of formula 9 wherein R is 3-methoxy-propyl: MS: 808 (API)

EXAMPLE 47

To a solution of the compound of formula 4 wherein $R^4$ is benzyloxycarbonyl (0.520 g, 0.6 mmol) in DME (6 mL) and TMEDA (2 mL) at −40° C. was added propynyl lithium (0.414 g, 9.0 mmol). After stirring at −40° C. for 2.5 hours, the reaction mixture was diluted with a saturated aqueous solution of ammonium chloride (30 mL) and EtOAc (30 mL). After separation, the aqueous layer was washed with EtOAc (3×10 mL). The combined organic extracts were washed with a saturated aqueous solution of sodium bicarbonate (25 mL) and brine (30 mL), dried over $Na_2SO_4$ and concentrated under vacuum. Silica gel chromatography with $MeOH:CH_2Cl_2:NH_4OH$ (4:95.6:0.4 to 6:93.6:0.4) afforded 0.157 g (29% yield) of the faster eluting diastereomer, along with 0.071 g (13% yield) of the slower eluting diastereomer and 0.070 (13% yield) of a mixture of the diastereomers.

A solution of the faster eluting diastereomer (0.157 g, 0.17 mmol) in MeOH (5 mL) was allowed to stir at 30° C. for 6 days. Upon concentration under vacuum, silica gel chromatography with $MeOH:CH_2Cl_2:NH_4OH$ (4:95.6:0.4 to 6:93.6:0.4) afforded 0.102 g (78% yield) of the compound of formula 9 wherein R is 1-propynyl according to the following configuration at the C-4" carbon (MS: 774 (API)):

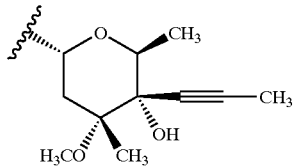

A solution of the slower eluting diastereomer (0.071 g, 0.078 mmol) in MeOH (3 mL) was allowed to stir at 30° C. for 6 days. Upon concentration under vacuum, silica gel chromatography with $MeOH:CH_2Cl_2:NH_4OH$ (4:95.6:0.4 to 6:93.6:0.4) afforded 0.041 g (68% yield) of material identical to that described by the compound of Example 41 which corresponds to the compound of formula 9 wherein R is 1-propynyl according to the following configuration at the C-4" carbon (MS: 774 (API)):

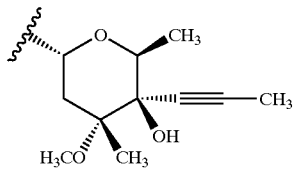

EXAMPLE 48

To a suspension of trimethyisulfonium tetrafluoroborate (1.03 g, 6.3 mmol) in THF (40 mL) at −10° C. was added KHMDS (120 g, 6.0 mmol). After stirring below 0° C. for 0.5 hour, the reaction vessel was cooled to −78° C. and a solution of the compound of formula 4 wherein $R^{13}$ is benzyloxycarbonyl (2.60 g, 3 mmol) in DME (10 mL) was added. After 0.5 hour, the reaction mixture was diluted with a saturated aqueous solution of ammonium chloride (40 mL) and EtOAc (50 mL). After separation, the aqueous layer was washed with EtOAc (3×30 mL). The combined organic extracts were washed with brine (40 mL), dried over $Na_2SO_4$ and concentrated under vacuum. Silica gel chromatography with $MeOH:CH_2Cl_2:NH_4OH$ (2:97.6:0.4 to 4:95.5:0.4) afforded 0.834 g (32% yield) of the compound of formula 5 wherein $R^4$ is benzyloxycarbonyl (MS: 881 (API)).

EXAMPLE 49

A solution of the compound of Example 48 (0.176 g, 0.2 mmol) in MeOH (5 mL) was allowed to stir at 50° C. for 4 days. Upon concentration, silica gel chromatography with $MeOH:CH_2Cl_2:NH_4OH$ (4:95.6:0.4 to 6:93.5:0.4) afforded 0.107 g (72% yield) of the compound of formula 5 wherein $R^4$ is hydrogen and the epoxide moiety at C-4" has the following configuration (MS: 748 (API)):

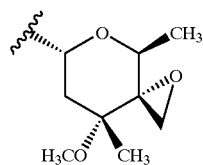

EXAMPLE 50

A solution of the compound of Example 48 (0.176 g, 0.2 mmol), potassium iodide (2.32 g, 14 mmol) and cyclopropylamine (2.43 mL, 2.00 g, 35 mmol) in MeOH (30 mL) was allowed to stir at 50° C. for 2 days. Upon concentration, the residue was dissolved in water (50 mL) and EtOAc (100 mL). After separation, the aqueous layer was washed with EtOAc (3×50 mL). The combined organic extracts were washed with a saturated aqueous solution of sodium bicarbonate (50 mL) and brine (40 mL), dried over $Na_2SO_4$ and concentrated under vacuum. Silica gel chromatography with $MeOH:CH_2Cl_2:NH_4OH$ (4:95.6:0.4 to 6:93.5:0.4) afforded 0.377 g (69% yield) of the compound of formula 9 wherein R is cyclopropylaminomethyl according to the following configuration at the C-4" carbon (MS: 805 (API)):

EXAMPLE 51

A solution of the compound of Example 48 (0.176 g, 0.2 mmol), tetrabutylammonium iodide (0.739 g, 2.0 mmol) and butylamine (0.395 mL, 0.293 g, 4 mmol) in MeOH (5 mL) was allowed to stir at 50° C. for 2 days. Upon concentration, the residue was dissolved in water (20 mL) and EtOAc (20 mL). After separation, the aqueous layer was washed with EtOAc (3×20 mL). The combined organic extracts were washed with brine (40 mL), dried over $Na_2SO_4$ and concentrated under vacuum. Silica gel chromatography with $MeOH:CH_2Cl_2:NH_4OH$ (4:95.6:0.4 to 6:93.5:0.4) afforded 0.088 g (54% yield) of the compound of formula 9 wherein R is propylaminomethyl according to the following configuration at the C-4" carbon (MS: 821 (API)):

EXAMPLE 52

To a solution of a compound of formula 4 wherein $R^4$ is benzyloxycarbonyl and the hydrogen attached to the C-9a nitrogen is replaced by benzyloxycarbonyl (0.500 g, 0.499 mmol) in THF (15 mL) 0° C. was added methylmagnesium bromide in $Et_2O$ (3.0 M, 1.2 mL). After 20 minutes, the reaction was diluted with EtOAc (30 mL) and water (50 mL). After separation, the aqueous layer was washed with EtOAc (3×35 mL). The combined organic extracts were washed with a 10% aqueous solution of sodium bicarbonate (100 mL) and brine (120 mL), dried over $Na_2SO_4$ and concentrated under vacuum to afford 0.500 g (98% yield) of an off-white foam. (MS: 1017, 845 (API)).

Palladium catalyst (0250 g, 10% Pd/C) was added to a solution of the compound described above (0.500 g 0.491 mmol) in isopropanol (50 mL). The reaction vessel was flushed and filled with hydrogen (50 psi) and shaken at room temperature for 48 hours. Additional palladium catalyst (0.250 g, 10% Pd/C) was added and hydrogenation was continued at 50 psi for 24 hours. The reaction mixture was filtered through Celite™ and concentrated under vacuum. The resulting oil was dissolved in isopropanol (50 mL), palladium catalyst was added (0.312 g, 10% Pd/C), and hydrogenation was continued at 50 psi for 24 hours. Additional palladium catalyst (0.170 g, 10% Pd/C) was added and hydrogenation was continued at 50 psi for 24 hours. The reaction mixture was filtered through Celite™ and concentrated under vacuum. Silica gel chromatography with $MeOH:CH_2Cl_2:NH_4OH$ (8:91:1 to 10:89:1) afforded 0.120 g (33% yield) of the compound of formula 9 wherein R is methyl according to the following configuration at the C-4" carbon (MS: 749 (API)):

EXAMPLE 53

To a solution of a compound of formula 4 wherein $R^4$ is benzyloxycarbonyl and the hydrogen attached to the C-9a nitrogen is replaced by benzyloxycarbonyl (0.101 g, 0.101 mmol) in THF (2 mL) at −78° C. was added phenylmagnesium bromide in THF (1.01 M, 1.0 mL). After 15 minutes, stirring was continued 0° C. for 1 hour, then at room temperature for 12 hours. The reaction was diluted with a 10% aqueous solution of sodium bicarbonate (10 mL) and EtOAc (20 mL). After separation, the aqueous layer was washed with EtOAc (3×15 mL). The combined organic extracts were washed with a 10% aqueous solution of sodium bicarbonate (20 mL) and brine (25 mL), dried over Na$_2$SO$_4$ and concentrated under vacuum. Silica gel chromatography with MeOH:CH$_2$Cl$_2$:NH$_4$OH (5:94:1 to 25:74:1) afforded 0.048 g (45% yield) of a white foam (MS: 1080 (LSIMS)).

Palladium catalyst (0.024 g, 10% Pd/C) was added to a solution of the compound described above (0.024 g, 0.022 mmol) in methanol (15 mL). The reaction vessel was flushed and filled with hydrogen (50 psi) and shaken at room temperature for 24 hours. The reaction mixture was filtered through Celite™ and concentrated under vacuum. Silica gel chromatography with MeOH:CH$_2$Cl$_2$:NH$_4$OH (5:94.5:1 to 10:89:1) afforded 0.010 g (28% yield) of the compound of formula 9 wherein R is phenyl: MS: 811 (LSIMS).

EXAMPLE 54

To a solution of the starting compound used in Example 53 (0.300 g, 0.30 mmol) in THF (3 mL) at 0° C. was added n-butylmagneslum chloride in THF (2.0 M, 1.5 mL). After 20 minutes the reaction was diluted with water and EtOAc (20 mL). After separation, the aqueous layer was washed with EtOAc (3×50 mL). The combined organic extracts were washed with a 10% aqueous solution of sodium bicarbonate (50 mL) and brine (55 mL), dried over Na$_2$SO$_4$ and concentrated under vacuum to afford 0295 g (93% yield) of an off-white foam (MS: 1060 (FAB)).

Palladium catalyst (0.087 g, 10% Pd/C) was added to a solution of the compound described above (0.087 g, 0.082 mmol) in isopropanol (15 mL). The reaction vessel was flushed and filled with hydrogen (50 psi) and shaken at room temperature for 24 hours. Additional palladium catalyst (0.087 g, 10% Pd/C) was added and hydrogenation was continued at 50 psi for 60 hours. The reaction mixture was filtered through Celite™ and concentrated under vacuum. Silica gel chromatography with MeOH:CH$_2$Cl$_2$:NH$_4$OH (5:94.5:0.5 to 10:89:1) afforded 0.010 g (28% yield) of the compound of formula 9 wherein R is n-butyl: MS: 792 (API).

EXAMPLE 55

To a solution of the starting compound used in Example 53 (0.200 g, 0.20 mmol) in THF (2 mL) at 0° C. was added ethylmagnesium bromide in THF (1.0 M, 2.0 mL). After 20 minutes the reaction was diluted with water and EtOAc (20 mL). After separation, the aqueous layer was washed with EtOAc (3×30 mL). The combined organic extracts were washed with a 10% aqueous solution of sodium bicarbonate (50 mL) and brine (55 mL), dried over Na$_2$SO$_4$ and concentrated under vacuum. Silica gel chromatography with MeOH:CH$_2$Cl$_2$:NH$_4$OH (5:94.5:0.5 to 20:79:1) afforded 0.079 g (38% yield) of a white foam (MS: 1033 (LSIMS)).

Palladium catalyst (0.035 g, 10% Pd/C) was added to a solution of the compound described above (0.079 g, 0.077 mmol) in ethanol (20 mL). The reaction vessel was flushed and filled with hydrogen (50 psi) and shaken at room temperature for 24 hours. Additional palladium catalyst (0.036 g, 10% Pd/C) was added and hydrogenation was continued at 50 psi for 24 hours. The reaction mixture was filtered through Celite™ and concentrated under vacuum, affording 0.056 g (96% yield) of the compound of formula 9 wherein R is ethyl: MS: 763 (TS).

EXAMPLE 56

To a solution of the starting compound used in Example 53 (0.300 g, 0.30 mmol) in THF (3 mL) at 0° C. was added isopropenylmagnesium chloride in THF (0.5 M, 6.0 mL). After 20 minutes the reaction was diluted with water and EtOAc (20 mL). After separation, the aqueous layer was washed with EtOAc (3×30 mL). The combined organic extracts were washed with a 10% aqueous solution of sodium bicarbonate (50 mL) and brine (55 mL), dried over Na$_2$SO$_4$ and concentrated under vacuum. Silica gel chromatography with MeOH:CH$_2$Cl$_2$:NH$_4$OH (3:96.9:0.1 to 20:79.9:0.1) afforded 0.063 g (20% yield) of a white foam (MS: 1045 (LSIMS)).

Palladium catalyst (0.075 g, 10% Pd/C) was added to a solution of the compound described above (0.150 g, 0.165 mmol) in ethanol (30 mL). The reaction vessel was flushed and filled with hydrogen (50 psi) and shaken at room temperature for 24 hours. Additional palladium catalyst (0.075 g, 10% Pd/C) was added and hydrogenation was continued at 50 psi for 24 hours. The reaction mixture was filtered through Celite™ and concentrated under vacuum. Silica gel chromatography with MeOH:CH$_2$Cl$_2$:NH$_4$OH (6:93:1 to 10:89:1) afforded 0.024 g (19% yield) of the compound of formula 9 wherein R is isopropenyl: MS: 775 (TS).

EXAMPLE 57

To a solution of the starting compound used in Example 53 (0.750 g, 0.75 mmol) in THF (12 mL) at 0° C. was added allylmagnesium chloride in THF (2.0 M, 3.0 mL). After 15 minutes the reaction was diluted with water and EtOAc (40 mL). After separation, the aqueous layer was washed with EtOAc (3×50 mL). The combined organic extracts were washed with a 10% aqueous solution of sodium bicarbonate (100 mL) and brine (100 mL), dried over Na$_2$SO$_4$ and concentrated under vacuum. Silica gel chromatography with MeOH:CH$_2$Cl$_2$:NH$_4$OH (6:93:1 to 15:84:1) afforded 0.530 g (68% yield) of an off-white foam (MS: 1044, 910 (API)).

Palladium catalyst (0.175 g, 10% Pd/C) was added to a solution of the compound described above (0.350 g, 0.335 mmol) in isopropanol (100 mL). The reaction vessel was flushed and filled with hydrogen (50 psi) and shaken at room temperature for 24 hours. Additional palladium catalyst (0.150 g, 10% Pd/C) was added and hydrogenation was continued at 50 psi for 24 hours. The reaction mixture was filtered through Celite™ and concentrated under vacuum. Silica gel chromatography with MeOH:CH$_2$Cl$_2$:NH$_4$OH (6:93:1 to 10:89:1) afforded 0.148 g (57% yield) of the compound of formula 9 wherein R is propyl: MS: 778 (API).

EXAMPLE 58

To a solution of the compound used as a starting material in Example 53 (0.750 g, 0.75 mmol) in THF (12 mL) at 0° C. was added allylmagnesium chloride in THF (2.0 M, 3.0 mL). After 15 minutes the reaction was diluted with water and EtOAc (40 mL). After separation, the aqueous layer was washed with EtOAc (3×50 mL). The combined organic extracts were washed with a 10% aqueous solution of sodium bicarbonate (100 mL) and brine (100 mL), dried over Na$_2$SO$_4$ and concentrated under vacuum. Silica gel chromatography with MeOH:CH$_2$Cl$_2$:NH$_4$OH (6893:1 to 15:84:1) afforded 0.530 g (68% yield) of an off-white foam (MS: 1044 (API)).

A solution of the compound described above (0.104 g, 0.100 mmol) and (1S)-(+)-10-camphor sulfonic acid (0.046 g, 0.200 mmol) in MeOH (4 mL) was cooled to −78° C. and treated with ozone until a deep blue color persisted. The reaction was purged with oxygen, dimethylsulfide (0.13 mL, 1.76 mmol) and pyridine (0.20 mL, 2.42 mmol) were added and stirring was continued for 12 hours. $CH_2Cl_2$ (30 mL) and 10% aqueous solution of sodium bicarbonate (10 mL) were added, the layers were separated and the aqueous layer was extracted with $CH_2Cl_2$ (3×30 mL). The combined organic extracts were washed with a 10% aqueous solution of sodium bicarbonate (50 mL) and brine (50 mL), dried over $Na_2SO_4$ and concentrated under vacuum. Silica gel chromatography with $MeOH:CH_2Cl_2:NH_4OH$ (6:93:1 to 10:89:1) afforded 0.024 g (23% yield) of an off-white foam (MS: 912 (API)).

To a solution of the compound described above (0.022 g, 0.024 mmol) in MeOH (1 mL) was added sodium borohydride (0.001 g, 0.024 mmol). Additional sodium borohydride (0.004 g, 1.00 mmol) was added over a period of 3 hours. The reaction mixture was diluted with $CH_2Cl_2$ (30 mL) and 10% sodium bicarbonate solution (20 mL). After separation, the aqueous layer was extracted with $CH_2Cl_2$ (3×30 mL). The combined organic extracts were washed with a 10% aqueous solution of sodium bicarbonate (50 mL) and brine (50 mL), dried over $Na_2SO_4$ and concentrated under vacuum to afford 0.022 9 (100% yield) of a yellow foam (MS: 914 (API)).

Palladium catalyst (0.012 g, 10% Pd/C) was added to a solution of the compound described above (0.022 g, 0.024 mmol) in isopropanol (10 mL). The reaction vessel was flushed and filled with hydrogen (50 psi) and shaken at room temperature for 24 hours. Additional palladium catalyst (0.020 g, 10% Pd/C) was added and hydrogenation was continued at 50 psi for 24 hours. The reaction mixture was filtered through Celite™ and concentrated under vacuum. Silica gel chromatography with $MeOH:CH_2Cl_2:NH_4OH$ (8:91:1 to 10:89:1) afforded 0.005 mg (23% yield) of the compound of formula 9 wherein R is 2-hydroxyethyl: MS: 779 (API).

EXAMPLE 59

To a solution of the starting compound used in Example 53 (0.750 g, 0.75 mmol) in THF (12 mL) at 0° C. was added allylmagnesium chloride in THF (2.0 M, 3.0 mL). After 15 minutes the reaction was diluted with water and EtOAc (40 mL). After separation, the aqueous layer was washed with EtOAc (3×50 mL). The combined organic extracts were washed with a 10% aqueous solution of sodium bicarbonate (100 mL) and brine (100 mL), dried over $Na_2SO_4$ and concentrated under vacuum. Silica gel chromatography with $MeOH:CH_2Cl_2:NH_4OH$ (6:93:1 to 15:84:1) afforded 0.530 g (68% yield) of an off-white foam (MS: 1044 (API)).

A solution of the compound described above (0.104 g, 0.100 mmol) and (1S-(+)-10-camphor sulfonic acid (0.046 g, 0.200 mmol) in MeOH (4 mL) was cooled to −78° C. and treated with ozone until a deep blue color persisted. The reaction was purged with oxygen, dimethylsulfide (0.13 mL, 1.76 mmol) and pyridine (0.20 mL, 2.42 mmol) were added and stirring was continued for 12 hours. $CH_2Cl_2$ (30 mL) and 10% aqueous solution of sodium bicarbonate (10 mL) were added, the layers were separated and the aqueous layer was extracted with $CH_2Cl_2$ (3×30 mL). The combined organic extracts were washed with a 10% aqueous solution of sodium bicarbonate (50 mL) and brine (50 mL), dried over $Na_2SO_4$ and concentrated under vacuum. Silica gel chromatography with $MeOH:CH_2Cl_2:NH_4OH$ (6:93:1 to 10:89:1) afforded 0.024 g (23% yield) of an off-white foam (MS: 912 (API)).

Palladium catalyst (0.040 g, 10% Pd/C) was added to a solution of the compound described above (0.057 g, 0.063 mmol) in isopropanol (15 mL). The reaction vessel was flushed and filled with hydrogen (50 psi) and shaken at room temperature for 24 hours. Additional palladium catalyst (0.040 g, 10% Pd/C) was added and hydrogenation was continued at 50 psi for 24 hours. The reaction mixture was filtered through Celite™ and concentrated under vacuum. Silica gel chromatography with $MeOH:CH_2Cl_2:NH_4OH$ (6:93:1 to 10:89:1) afforded 0.010 g (15% yield) of the compound of formula 9 wherein R is formylmethyl: MS: 777 (API).

EXAMPLE 60

To a solution of 2-bromopyridine (0.474 g, 3.0 mmol) in THF (5 mL) at −78° C. was added n-butyl lithium (3.0 M, 12 mL) at −78° C. After 40 minutes, the solution was transferred via a cannula cooled with a dry ice jacket to a flask containing $MgCl_2$ (0.428 g, 4.5 mmol) and ether (4 mL) at −78° C. After 15 minutes, a solution of a compound of formula 4 wherein $R^4$ is benzyloxycarbonyl (0.260 g, 0.3 mmol) in THF (3 mL) at −78° C. was introduced and stirring was continued allowing the reaction to warm to room temperature over several hours. After 3.5 hours, the reaction mixture was diluted with a saturated aqueous solution of sodium bicarbonate (20 mL) and EtOAc (30 mL). After separation, the aqueous layer was washed with EtOAc (3×50 mL). The combined organic extracts were washed with a saturated aqueous solution of sodium bicarbonate (50 mL) and brine (60 mL), dried over $Na_2SO_4$ and concentrated under vacuum. Silica gel chromatography with $MeOH:CH_2Cl_2:NH_4OH$ (6:93.3:0.7 to 10:89:1) afforded 0.023 g (9.5% yield) of the compound of formula 9 wherein R is 2-pyridyl: MS: 812 (API).

EXAMPLE 61

To a round bottom flask containing n-butyl lithium (3.0 M, 1.62 mL) in diethyl ether (15 mL) at −78° C. was added chilled (−78° C.) 3-bromopyridine (0.790 g, 5 mmol) via a carmula cooled with a dry ice jacket. Stirring continued at −78° C. for 35 minutes. A suspension of $MgBr_2$ diethyl ethereate (0.114 g, 0.440 mmol) in diethyl ether (3 mL) at −78° C. was added via a cannula cooled with a dry ice jacket to the 3-pyridyl lithium solution. A solution of a compound of formula 4 wherein $R^4$ is benzyloxycarbonyl (0.347 g, 0.400 mmol) in diethyl ether (3 mL) at −78° C. was introduced via cannula. Stirring continued at −78° C. for 2 hours and slowly allowed to warm to 0° C. over 3 hours. The reaction mixture was diluted with a saturated aqueous solution of sodium bicarbonate (20 mL) and EtOAc (30 mL). After separation, the aqueous layer was washed with EtOAc (3×50 mL). The combined organic extracts were washed with a saturated aqueous solution of sodium bicarbonate (50 mL) and brine (60 mL), dried over $Na_2SO_4$ and concentrated under vacuum. Silica gel chromatography with $MeOH:CH_2Cl_2:NH_4OH$ (4:95.4:0.6 to 20:79:1) afforded 0.075 g (26% yield) of a white foam (MS: 947,812 (API)).

Palladium catalyst (0.073 g, 10% Pd/C) was added to a solution of the compound described above (0.073 g, 0.077 mmol) in isopropanol (30 mL). The reaction vessel was flushed and filled with hydrogen (50 psi) and shaken at room temperature for 48 hours. The reaction mixture was filtered through Celite™ and concentrated under vacuum. Silica gel chromatography with $MeOH:CH_2Cl_2:NH_4OH$ (6:93:1 to 8:91:1) afforded 0.032 g (51% yield) of the compound of formula 9 wherein R is 3-pyridyl: MS: 812 (API).

EXAMPLE 62

To a solution of methyl magnesium bromide in diethyl ether (3.0 M, 1.8 mL) at 0° C. was added a solution of 5-hexynenitrile (0.63 mL, 6.00 mmol) in THF (5 mL). After stirring at 0° C. for 6 hours, a solution of the compound of formula 4 wherein $R^4$ is H (0.220 g, 0.300 mmol) in DME (10 mL) was added and stirring was continued at 0° C. for 0.5 hour, then at room temperature for 4 hours. The reaction mixture was diluted with water (20 mL) and EtOAc (25 mL), the layers were separated and the aqueous layer was washed with EtOAc (3×20 mL). The combined organic extracts were washed with a saturated aqueous solution of sodium bicarbonate (20 mL) and brine (25 mL), dried over $Na_2SO_4$ and concentrated under vacuum. Silica gel chromatography with $MeOH:CH_2Cl_2:NH_4OH$ (6:93:1 to 10:89:1) afforded 0.035 g (14% yield) of the compound of formula 9 wherein R is 6-cyano-1-pentynyl: MS: 827 (API).

EXAMPLE 63

To a solution of the compound of Example 49, except wherein $R^4$ is benzyloxycarbonyl, (0.101 g, 0.115) in DME (3 mL) was added $LiAlH_4$ (1.0 M, 2.1 mL) dropwise. After 10 minutes the reaction mixture was treated sequentially with water (0.044 mL), 15% NaOH solution (0.044 mL), and water (0.132 mL), then stirred at rt for 0.5 hour. The mixture was diluted with EtOAc (20 mL) and water (20 mL). After separation the aqueous layer was extracted with EtOAc (3×30 mL). The combined organic extracts were washed with a saturated aqueous solution of sodium bicarbonate (50 mL) and brine (60 mL), dried over $Na_2SO_4$ and concentrated under vacuum. Silica gel chromatography with $MeOH:CH_2Cl_2:NH_4OH$ (3:96.5:0.5 to 3.5:95:0.5) afforded 0.042 g (49% yield) of the compound of formula 9 wherein R is methyl according to the following configuration at the C-4" carbon (MS: 749 (API)):

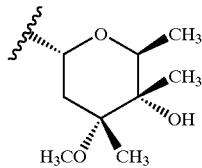

EXAMPLE 64

To a solution of 1-methylimidazole (0.41 g, 4.99 mmol) in THF (5 ml) at −78° C. was added n-butyl lithium (2.5 M, 2.02 ml). After 45 minutes at −78° C. the solution was added via cannula to a flask containing $MgCl_2$ (0.71 g, 7.49 mmol) and THF (5 mL) at 0° C. After 1.5 hours at 0° C. a solution of the starting compound used in Example 53 (0.500 g, 0.499 mmol) in DME (2 mL) was introduced and stirring was continued at 0° C. for 1 hour. The reaction mixture was diluted with a saturated aqueous solution of sodium bicarbonate (100 mL) and EtOAc (100 mL). After separation, the aqueous layer was washed with EtOAc (3×100 mL). The combined organic extracts were washed with a saturated aqueous solution of sodium bicarbonate (100 mL) and brine (100 mL), dried over $Na_2SO_4$ and concentrated under vacuum to afford 0.660 g of a yellow foam (MS: 949 (API)).

Palladium catalyst (0.700 g, 10% Pd/C) was added to a solution of the compound described above in isopropanol (60 mL). The reaction vessel was flushed and filled with hydrogen (50 psi) and shaken at room temperature for 24 hours. Addtional palladium catalyst (0.500 g, 10% Pd/C) was added and hydrogenation was continued at 50 psi for 24 hours. The reaction mixture was filtered through Celite™ and concentrated under vacuum. Silica gel chromatography with $MeOH:CH_2Cl_2:NH_4OH$ (1:98:1 to 8:91:1) afforded 0.052 g (13% yield) of the compound of formula 9 wherein R is 1-methylimidazol-2-yl: MS: 816 (API).

EXAMPLE 65

To a solution of furan (0.34 g, 4.99 mmol) in THF (5 ml) at −78° C. was added n-butyl lithium (2.5 M, 1.98 ml). After 0.5 hour at −78° C. the solution was added to a flask containing $MgCl_2$ (0.71 g, 7.49 mmol) and THF (5 mL) at 0° C. After 1.5 hours at 0° C., a solution of the starting compound used in Example 53 (0.500 g, 0.499 mmol) in DME (2 mL) was introduced and stirring was continued at 0° C. for 1 hour, then at room temperature for 1 hour. The reaction mixture was diluted with a saturated aqueous solution of sodium bicarbonate (100 mL) and EtOAc (100 mL). After separation, the aqueous layer was washed with EtOAc (3×100 mL). The combined organic extracts were washed with a saturated aqueous solution of sodium bicarbonate (100 mL) and brine (100 mL), dried over $Na_2SO_4$ and concentrated under vacuum. Silica gel chromatography with $MeOH:CH_2Cl_2:NH_4OH$ (1:98:1 to 8:91:1) afforded 0.096 g (24% yield) of a white foam (MS: 935 (API)).

Palladium catalyst (0.100 g, 10% Pd/C) was added to a solution of the compound described above in isopropanol (15 mL). The reaction vessel was flushed and filled with hydrogen (50 psi) and shaken at room temperature for 72 hours. The reaction mixture was filtered through Celite™ and concentrated under vacuum. Silica gel chromatography with $MeOH:CH_2Cl_2:NH_4OH$ (1:98:1 to 8:91:1) afforded 0.053 g (13% yield) of the compound of formula 9 wherein R is 2-furyl: MS: 802 (API).

EXAMPLE 66

To a solution of N-methylpyrrole (0.184 g, 2.31 mmol) in THF (4 ml) at −78° C. was added n-butyl lithium (2.5 M, 0.93 ml). The solution was warmed to room temperature over 1 hour and then added via cannula to a flask containing $MgCl_2$ (0.329 g, 3.46 mmol) and $Et_2O$ (4 mL) at room temperature. After 1 hour, a solution of the compound of formula 4 wherein $R^4$ is benzytoxycarbonyl (0.200 g, 0231 mmol) In THF (2 mL) was introduced and stirring was continued at room temperature for 45 minutes. The reaction mixture was diluted with a saturated aqueous solution of sodium bicarbonate (50 mL) and EtOAc (50 mL). After separation, the aqueous layer was washed with EtOAc (3×50 mL). The combined organic extracts were washed with a saturated aqueous solution of sodium bicarbonate (50 mL) and brine (50 mL), dried over $Na_2SO_4$ and concentrated under vacuum to afford 0293 g of a yellow foam (MS: 949 (API)).

Palladium catalyst (0.324 g, 10% Pd/C) was added to a solution of the compound described above in isopropanol (30 mL). The reaction vessel was flushed and filled with hydrogen (50 psi) and shaken at room temperature for 24 hours. Additional palladium catalyst (0.300 g, 10% Pd/C) was added and hydrogenation was continued at 50 psi for 24 hours. The reaction mixture was filtered through Celite™ and concentrated under vacuum. Silica gel chromatography with $MeOH:CH_2Cl_2:NH_4OH$ (6:93:1 to 8:91:1) afforded 0.033 g (18% yield) of the compound of formula 9 wherein R is 1-methyl2-pyrrolyl: MS: 814 (API).

EXAMPLE 67

To a solution of unpurified compound prepared as described in Example 39 (0.480 g) in isopropanol (40 mL) was added platinum oxide (0.115 g, 0.505 mmol). The reaction vessel was flushed and filled with hydrogen (50 psi) and shaken at room temperature for 24 hours. Filtration of an aliquot of the reaction mixture through Celite™ and concentration under vacuum afforded the compound of formula 9 wherein R is 3-dimethylamino-1-propenyl: MS: 819 (API).

EXAMPLE 68

Platinum oxide (0.076 g, 0.335 mmol) was added to the remaining solution from Example 67 and the reaction vessel was flushed and filled with hydrogen (50 psi) and shaken at room temperature for 96 hours. The reaction mixture was filtered through Celite™ and concentrated under vacuum. Silica gel chromatography with $MeOH:CH_2Cl_2:NH_4OH$ (4:95:1 to 6:93:1) afforded 0.069 g (15% yield) of the compound of formula 9 wherein R is 3-dimethylpropyl: MS: 821 (API).

TABLE 2

The compounds of Examples 69–81 have the general structure of formula 10 below with the R substituents indicated in the table below. The compounds of Examples 69–82 were prepared following the procedures of Examples 50 and 51, referred to above, with the reaction period specified in the table below. In the table, the yield and mass spectra ("Mass Spec") data apply to the final product.

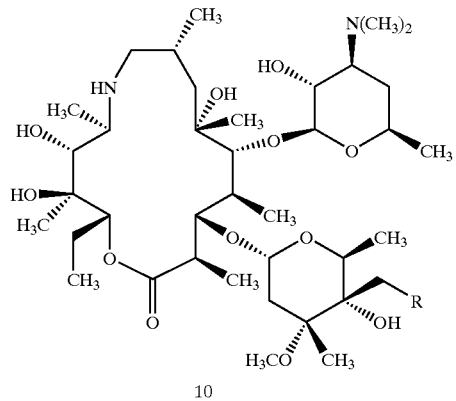

10

| Example | R | Reaction Time (hours) | Yield (%) | Mass Spec |
|---|---|---|---|---|
| 69 | 1-imidazolyl | 72 | 60 | 816 |
| 70 | n-propylamino | 48 | 55 | 807 |
| 71 | dimethylamino | 24 | 42 | 793 |
| 72 | methylamino | 120 | 55 | 779 |
| 73 | ethylamino | 120 | 58 | 793 |
| 74 | isopropylamino | 48 | 44 | 806 |
| 75 | isobutylamino | 48 | 27 | 821 |
| 76 | trimethyleneimino | 24 | 31 | 804 |
| 77 | allylamino | 24 | 22 | 804 |
| 78 | cyclopropylmethylamino | 24 | 34 | 818 |
| 79 | N-ethylmethylamino | 48 | 16 | 820 |
| 80 | t-butylamino | 96 | 30 | 821 |
| 81 | diethylamino | 168 | 25 | 820 |
| 81(a) | pyrrolidinyl | 48 | 75 | 818.5 |
| 81(b) | piperidinyl | 96 | 95 | 832.6 |

TABLE 2-continued

| | | | | |
|---|---|---|---|---|
| 82 | 4-methoxybenzylamino | 48 | 21.7 | 884.6 |
| 83 | 4-nitrobenzylamino | 48 | 8 | 899.7 |
| 84 | 4-chlorobenzylamino | 48 | 25.5 | 888.6 |
| 85 | 3,4-difluorobenzylamino | 48 | 14.5 | 890.6 |
| 85 | 3-pyridylmethylamino | 48 | 21.0 | 855.6 |
| 86 | 4-trifluoromethylbenzyl-amino | 48 | 16.5 | 922.6 |
| 87 | 2,6-difluorobenzylamino | 48 | 11.0 | 890.6 |
| 88 | benzylamino | 96 | 62 | 854.7 |
| 89 | 4-fluorobenzylamino | 48 | 50.9 | 872.7 |
| 90 | 3-fluorobenzylamino | 48 | 32.7 | 872.7 |
| 91 | 2-fluorobenzylamino | 48 | 39.6 | 872.7 |
| 92 | 2,4-difluorobenzylamino | 48 | 24.6 | 890.1 |
| 93 | 2,5-difluorobenzylamino | 48 | 28.1 | 890.1 |
| 94 | 3,5-difluorobenzylamino | 48 | 35.6 | 890.1 |
| 95 | 1-(4-fluorophenyl)-piperazine | 48 | 44.7 | 927.6 |
| 96 | 2-trifluoromethylbenzyl-amino | 48 | 32.7 | 922.5 |
| 97 | 4-trifluoromethylbenzyl-amino | 48 | 28.6 | 938.1 |
| 98 | 3-trifluoromethylbenzyl-amino | 48 | 26.2 | 922.6 |
| 99 | 2-fluorophenylethyl-amino | 48 | 33.5 | 886.2 |
| 100 | 3-fluorophenylethyl-amino | 48 | 28.7 | 886.1 |
| 101 | 4-pyridylmethylamino | 48 | 46 | 855.2 |
| 102 | methyl,3-pyridylmethyl-amino | 72 | 28.8 | 869.6 |
| 103 | 4-hydroxy-3-methoxybenzylamino | 48 | 12.0 | 900.1 |
| 104 | piperonylamino | 48 | 14.0 | 898.1 |
| 105 | 3-methoxybenzylamino | 48 | 33.0 | 884.1 |
| 106 | 2-methoxybenzylamino | 48 | 24.0 | 884.5 |
| 107 | 2-pyridylmethylamino | 48 | 28.9 | 855.1 |

What is claimed is:
1. A method of treating a bacterial infection or a protozoal infection in a mammal, fish, or bird which comprises administering to said mammal, fish or bird a therapeutically effective amount of the formula

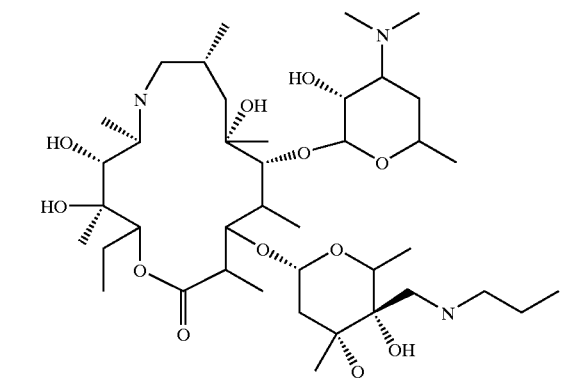

or a pharmaceutically acceptable salt thereof.

* * * * *